United States Patent
Chang et al.

(10) Patent No.: US 7,686,013 B2
(45) Date of Patent: *Mar. 30, 2010

(54) VARIABLE RESISTANCE PULMONARY VENTILATION BYPASS VALVE

(75) Inventors: Asia Chang, Saratoga, CA (US); Don Tanaka, Saratoga, CA (US)

(73) Assignee: Portaero, Inc., Cupertino, CA (US)

( * ) Notice: Subject to any disclaimer, the term of this patent is extended or adjusted under 35 U.S.C. 154(b) by 176 days.

This patent is subject to a terminal disclaimer.

(21) Appl. No.: 12/029,552

(22) Filed: Feb. 12, 2008

(65) Prior Publication Data

US 2008/0127982 A1 Jun. 5, 2008

Related U.S. Application Data

(63) Continuation of application No. 11/332,977, filed on Jan. 17, 2006, now Pat. No. 7,406,963.

(51) Int. Cl.
*A61M 11/00* (2006.01)

(52) U.S. Cl. ............................ 128/200.24; 128/207.14; 128/200.16

(58) Field of Classification Search ............ 128/200.24, 128/200.26, 207.14, 207.15, 207.16
See application file for complete search history.

(56) References Cited

U.S. PATENT DOCUMENTS

| | | |
|---|---|---|
| 733,152 A | 7/1903 | Chisholm |
| 953,922 A | 4/1910 | Rogers |
| 2,206,687 A | 7/1940 | Bloomheart |
| 2,867,213 A | 1/1959 | Thomas, Jr. |
| 2,873,742 A | 2/1959 | Shelden |
| 2,991,787 A | 7/1961 | Shelden et al. |
| 3,253,594 A | 5/1966 | Matthews et al. |
| 3,384,087 A | 5/1968 | Brummelkamp |
| 3,463,159 A | 8/1969 | Heimlich |
| 3,511,243 A | 5/1970 | Toy |
| 3,556,103 A | 1/1971 | Calhoun et al. |
| 3,638,649 A | 2/1972 | Ersek |
| 3,682,166 A | 8/1972 | Jacobs |
| 3,688,773 A | 9/1972 | Weiss |
| 3,777,757 A | 12/1973 | Gray et al. |

(Continued)

FOREIGN PATENT DOCUMENTS

EP         0260543 A1     3/1988

(Continued)

OTHER PUBLICATIONS

Al-Salem et al., "Computed tomography-guided percutaneous needle aspiration of lung abscesses in neonates and children", Pediatr Surg Int (1997) 12: 417-419, copyright Springer-Verlag 1997.

(Continued)

*Primary Examiner*—Steven O Douglas
(74) *Attorney, Agent, or Firm*—Fliesler Meyer LLP

(57) ABSTRACT

A collateral ventilation bypass trap system directly linked with a patient's lung or lungs may be utilized to increase the expiratory flow from the diseased lung or lungs, thereby treating one aspect of chronic obstructive pulmonary disease. The system includes a trap, a filter/one-way valve, an air carrying conduit and a retention device for securing system elements in position. The system also includes a flow restriction device for controlling the flow of air through the air carrying conduit.

19 Claims, 10 Drawing Sheets

U.S. PATENT DOCUMENTS

| | | |
|---|---|---|
| 3,788,326 A | 1/1974 | Jacobs |
| 3,817,250 A | 6/1974 | Weiss et al. |
| 3,908,704 A | 9/1975 | Clement et al. |
| 3,916,903 A | 11/1975 | Pozzi |
| 4,153,058 A | 5/1979 | Nehme |
| 4,291,694 A | 9/1981 | Chai |
| 4,439,189 A | 3/1984 | Sargeant et al. |
| 4,465,062 A | 8/1984 | Versaggi et al. |
| 4,502,482 A | 3/1985 | DeLuccia et al. |
| 4,583,977 A | 4/1986 | Shishov et al. |
| 4,664,660 A | 5/1987 | Goldberg et al. |
| 4,799,494 A | 1/1989 | Wang |
| 4,813,929 A | 3/1989 | Semrad |
| 4,826,495 A | 5/1989 | Petersen |
| 4,828,553 A | 5/1989 | Nielsen |
| 4,869,717 A | 9/1989 | Adair |
| 4,872,869 A | 10/1989 | Johns |
| 4,889,534 A | 12/1989 | Mohiuddin et al. |
| 4,931,045 A | 6/1990 | Steer |
| 4,944,724 A | 7/1990 | Goldberg et al. |
| 4,959,054 A | 9/1990 | Heimke et al. |
| 4,976,688 A | 12/1990 | Rosenblum |
| 5,004,456 A | 4/1991 | Botterbusch et al. |
| 5,060,645 A | 10/1991 | Russell |
| 5,078,689 A | 1/1992 | Keller |
| 5,137,509 A | 8/1992 | Freitas |
| 5,139,485 A | 8/1992 | Smith et al. |
| 5,218,957 A | 6/1993 | Strickland |
| 5,230,332 A | 7/1993 | Strickland |
| 5,230,350 A | 7/1993 | Fentress |
| 5,261,708 A | 11/1993 | Steer |
| 5,263,939 A | 11/1993 | Wortrich |
| 5,312,331 A | 5/1994 | Knoepfler |
| 5,315,992 A | 5/1994 | Dalton |
| 5,336,206 A | 8/1994 | Shichman |
| 5,354,283 A | 10/1994 | Bark et al. |
| 5,356,386 A | 10/1994 | Goldberg et al. |
| 5,366,478 A | 11/1994 | Brinkerhoff et al. |
| 5,370,625 A | 12/1994 | Shichman |
| 5,376,376 A | 12/1994 | Li |
| 5,389,077 A | 2/1995 | Melinyshyn et al. |
| 5,401,262 A | 3/1995 | Karwoski et al. |
| 5,431,633 A | 7/1995 | Fury |
| 5,478,333 A | 12/1995 | Asherman, Jr. |
| 5,496,297 A | 3/1996 | Olsen |
| 5,501,677 A | 3/1996 | Jensen |
| 5,501,678 A | 3/1996 | Olsen |
| 5,588,424 A | 12/1996 | Insler et al. |
| 5,616,131 A | 4/1997 | Sauer et al. |
| 5,660,175 A | 8/1997 | Dayal |
| 5,662,629 A | 9/1997 | Steer et al. |
| 5,728,066 A | 3/1998 | Daneshvar |
| 5,730,735 A | 3/1998 | Holmberg et al. |
| 5,738,661 A | 4/1998 | Larice |
| 5,807,341 A | 9/1998 | Heim |
| 5,830,200 A | 11/1998 | Steer et al. |
| 5,843,053 A | 12/1998 | Steer |
| 5,897,531 A | 4/1999 | Amirana |
| 5,931,821 A | 8/1999 | Weilbacher et al. |
| 5,954,636 A | 9/1999 | Schwartz et al. |
| 5,971,962 A | 10/1999 | Kojima et al. |
| 5,972,026 A | 10/1999 | Laufer et al. |
| 6,059,816 A | 5/2000 | Moenning |
| 6,083,255 A | 7/2000 | Laufer et al. |
| 6,174,323 B1 | 1/2001 | Biggs et al. |
| 6,197,010 B1 | 3/2001 | Leise, Jr. et al. |
| 6,200,333 B1 | 3/2001 | Laufer |
| 6,258,100 B1 | 7/2001 | Alferness et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,290 B1 | 9/2001 | Perkins et al. |
| 6,293,930 B1 | 9/2001 | Brunsgaard et al. |
| 6,293,951 B1 | 9/2001 | Alferness et al. |
| 6,299,633 B1 | 10/2001 | Laufer |
| 6,322,536 B1 | 11/2001 | Rosengart et al. |
| 6,328,689 B1 | 12/2001 | Gonzalez et al. |
| 6,330,882 B1 | 12/2001 | French |
| 6,334,441 B1 | 1/2002 | Zowtiak et al. |
| 6,358,269 B1 | 3/2002 | Aye |
| 6,398,775 B1 | 6/2002 | Perkins et al. |
| 6,402,754 B1 | 6/2002 | Gonzalez |
| 6,411,852 B1 | 6/2002 | Danek et al. |
| 6,416,554 B1 | 7/2002 | Alferness et al. |
| 6,432,100 B1 | 8/2002 | Affeld |
| 6,443,156 B1 | 9/2002 | Niklason et al. |
| 6,468,292 B1 | 10/2002 | Mollenauer et al. |
| 6,485,407 B2 | 11/2002 | Alferness et al. |
| 6,488,673 B1 | 12/2002 | Laufer et al. |
| 6,491,706 B1 | 12/2002 | Alferness et al. |
| 6,514,290 B1 | 2/2003 | Loomas |
| 6,517,519 B1 | 2/2003 | Rosen et al. |
| 6,520,183 B2 | 2/2003 | Amar |
| 6,527,761 B1 | 3/2003 | Soltesz et al. |
| 6,550,475 B1 | 4/2003 | Oldfield |
| 6,569,121 B1 | 5/2003 | Purow et al. |
| 6,569,166 B2 | 5/2003 | Gonzalez |
| 6,585,639 B1 | 7/2003 | Kotmel et al. |
| 6,589,161 B2 | 7/2003 | Corcoran |
| 6,592,594 B2 | 7/2003 | Rimbaugh et al. |
| 6,599,311 B1 | 7/2003 | Biggs et al. |
| 6,609,521 B1 | 8/2003 | Belani et al. |
| 6,629,951 B2 | 10/2003 | Laufer et al. |
| 6,632,239 B2 | 10/2003 | Snyder et al. |
| 6,632,243 B1 | 10/2003 | Zadno-Azizi et al. |
| 6,634,360 B1 | 10/2003 | Flodin |
| 6,634,363 B1 | 10/2003 | Danek et al. |
| 6,638,253 B2 | 10/2003 | Breznock |
| 6,653,525 B2 | 11/2003 | Ingenito et al. |
| 6,659,961 B2 | 12/2003 | Robinson |
| 6,679,264 B1 | 1/2004 | Deem et al. |
| 6,682,506 B1 | 1/2004 | Navarro |
| 6,692,494 B1 | 2/2004 | Cooper et al. |
| 6,694,979 B2 | 2/2004 | Deem et al. |
| 6,695,791 B2 | 2/2004 | Gonzalez |
| 6,709,401 B2 | 3/2004 | Perkins et al. |
| 6,712,812 B2 | 3/2004 | Roschak et al. |
| 6,736,797 B1 | 5/2004 | Larsen et al. |
| 6,749,606 B2 | 6/2004 | Keast et al. |
| 6,770,063 B2 | 8/2004 | Goldberg et al. |
| 6,770,070 B1 | 8/2004 | Balbierz |
| 6,790,172 B2 | 9/2004 | Alferness et al. |
| 6,827,086 B2 | 12/2004 | Shuman |
| 6,837,906 B2 | 1/2005 | Ginn |
| 6,840,243 B2 | 1/2005 | Deem et al. |
| 6,843,767 B2 | 1/2005 | Corcoran et al. |
| 6,849,061 B2 | 2/2005 | Wagner |
| 6,852,108 B2 | 2/2005 | Barry et al. |
| 6,860,847 B2 | 3/2005 | Alferness et al. |
| 6,878,141 B1 | 4/2005 | Perkins et al. |
| 6,886,558 B2 | 5/2005 | Tanaka |
| 6,901,927 B2 | 6/2005 | Deem et al. |
| 6,904,909 B2 | 6/2005 | Andreas et al. |
| 6,905,518 B2 | 6/2005 | Ginn |
| 6,916,310 B2 | 7/2005 | Sommerich |
| 6,929,637 B2 | 8/2005 | Gonzalez et al. |
| 6,941,950 B2 | 9/2005 | Wilson et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,014,628 B2 | 3/2006 | Bousquet |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |

| Patent/Pub No. | Date | Name |
|---|---|---|
| 7,086,398 B2 | 8/2006 | Tanaka |
| 7,100,616 B2 | 9/2006 | Springmeyer |
| 7,135,010 B2 | 11/2006 | Buckman et al. |
| 7,141,046 B2 | 11/2006 | Perkins et al. |
| 7,165,548 B2 | 1/2007 | Deem et al. |
| 7,172,581 B2 | 2/2007 | Ciok et al. |
| 7,175,644 B2 | 2/2007 | Cooper et al. |
| 7,182,772 B2 | 2/2007 | Alferness et al. |
| 7,186,259 B2 | 3/2007 | Perkins et al. |
| 7,192,420 B2 | 3/2007 | Whiteford |
| 7,195,016 B2 | 3/2007 | Loyd et al. |
| 7,195,017 B2 | 3/2007 | Tanaka |
| 7,207,946 B2 | 4/2007 | Sirokman |
| 7,232,414 B2 | 6/2007 | Gonzalez |
| 7,244,245 B2 | 7/2007 | Purow et al. |
| 7,252,086 B2 | 8/2007 | Tanaka |
| 2001/0025132 A1 | 9/2001 | Alferness et al. |
| 2001/0041906 A1 | 11/2001 | Gonzalez |
| 2001/0041932 A1 | 11/2001 | Scholz et al. |
| 2002/0042564 A1 | 4/2002 | Cooper et al. |
| 2002/0062120 A1 | 5/2002 | Perkins et al. |
| 2002/0077593 A1 | 6/2002 | Perkins et al. |
| 2002/0087153 A1 | 7/2002 | Roschak et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0165618 A1 | 11/2002 | Ingenito et al. |
| 2002/0188171 A1 | 12/2002 | Alferness et al. |
| 2003/0013935 A1 | 1/2003 | Alferness et al. |
| 2003/0018344 A1 | 1/2003 | Kaji et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0065339 A1 | 4/2003 | Snyder et al. |
| 2003/0069488 A1 | 4/2003 | Alferness et al. |
| 2003/0078469 A1 | 4/2003 | Corcoran |
| 2003/0083542 A1 | 5/2003 | Alferness et al. |
| 2003/0083671 A1 | 5/2003 | Rimbaugh et al. |
| 2003/0127090 A1 | 7/2003 | Gifford et al. |
| 2003/0130593 A1 | 7/2003 | Gonzalez |
| 2003/0149446 A1 | 8/2003 | Shuman |
| 2003/0154988 A1 | 8/2003 | DeVore et al. |
| 2003/0158515 A1 | 8/2003 | Gonzalez et al. |
| 2003/0163024 A1 | 8/2003 | Corcoran |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0186904 A1 | 10/2003 | Ruben et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0216730 A1 | 11/2003 | Barry et al. |
| 2003/0216769 A1 | 11/2003 | Dillard et al. |
| 2003/0228344 A1 | 12/2003 | Fields et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0016435 A1 | 1/2004 | Deem et al. |
| 2004/0024356 A1 | 2/2004 | Tanaka |
| 2004/0031494 A1 | 2/2004 | Danek et al. |
| 2004/0040555 A1 | 3/2004 | Tanaka |
| 2004/0047855 A1 | 3/2004 | Ingenito |
| 2004/0055606 A1 | 3/2004 | Hendricksen et al. |
| 2004/0059263 A1 | 3/2004 | DeVore et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078026 A1 | 4/2004 | Wagner |
| 2004/0078054 A1 | 4/2004 | Biggs et al. |
| 2004/0097983 A1 | 5/2004 | Snyder et al. |
| 2004/0143282 A1 | 7/2004 | Dillard et al. |
| 2004/0144387 A1 | 7/2004 | Amar |
| 2004/0158228 A1 | 8/2004 | Perkins et al. |
| 2004/0167636 A1 | 8/2004 | Dillard et al. |
| 2004/0173218 A1 | 9/2004 | Yamada et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0211412 A1 | 10/2004 | Alferness et al. |
| 2004/0211434 A1 | 10/2004 | Loomas et al. |
| 2004/0220446 A1 | 11/2004 | Corcoran et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0237966 A1 | 12/2004 | Tanaka |
| 2004/0243140 A1 | 12/2004 | Alferness et al. |
| 2004/0244802 A1 | 12/2004 | Tanaka |
| 2004/0244803 A1 | 12/2004 | Tanaka |
| 2005/0005936 A1 | 1/2005 | Wondka |
| 2005/0015106 A1 | 1/2005 | Perkins et al. |
| 2005/0022809 A1 | 2/2005 | Wondka |
| 2005/0025816 A1 | 2/2005 | Tanaka |
| 2005/0033310 A1 | 2/2005 | Alferness et al. |
| 2005/0033344 A1 | 2/2005 | Dillard et al. |
| 2005/0043745 A1 | 2/2005 | Alferness et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0066976 A1 | 3/2005 | Wondka |
| 2005/0085801 A1 | 4/2005 | Cooper et al. |
| 2005/0096529 A1 | 5/2005 | Cooper et al. |
| 2005/0103340 A1 | 5/2005 | Wondka |
| 2005/0107783 A1 | 5/2005 | Tom et al. |
| 2005/0131276 A1 | 6/2005 | Alferness et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0161040 A1 | 7/2005 | Tanaka |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178385 A1 | 8/2005 | Dellaca' et al. |
| 2005/0178389 A1 | 8/2005 | Shaw et al. |
| 2005/0192526 A1 | 9/2005 | Biggs et al. |
| 2005/0203483 A1 | 9/2005 | Perkins et al. |
| 2005/0205097 A1 | 9/2005 | Kyle, Jr. |
| 2005/0244401 A1 | 11/2005 | Ingenito |
| 2005/0281797 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |
| 2006/0025815 A1 | 2/2006 | McGurk et al. |
| 2006/0047291 A1 | 3/2006 | Barry |
| 2006/0076023 A1 | 4/2006 | Rapacki et al. |
| 2006/0095002 A1 | 5/2006 | Soltesz et al. |
| 2006/0107961 A1 | 5/2006 | Tanaka |
| 2006/0116749 A1 | 6/2006 | Willink et al. |
| 2006/0118125 A1 | 6/2006 | Tanaka |
| 2006/0118126 A1 | 6/2006 | Tanaka |
| 2006/0124126 A1 | 6/2006 | Tanaka |
| 2006/0130830 A1 | 6/2006 | Barry |

| | | | |
|---|---|---|---|
| 2006/0135947 A1 | 6/2006 | Soltesz et al. | |
| 2006/0135984 A1 | 6/2006 | Kramer et al. | |
| 2006/0142672 A1 | 6/2006 | Keast et al. | |
| 2006/0161233 A1 | 7/2006 | Barry et al. | |
| 2006/0162731 A1 | 7/2006 | Wondka et al. | |
| 2006/0206147 A1 | 9/2006 | DeVore et al. | |
| 2006/0212046 A1 | 9/2006 | Pearce et al. | |
| 2006/0212051 A1 | 9/2006 | Snyder et al. | |
| 2006/0235432 A1 | 10/2006 | DeVore et al. | |
| 2006/0235467 A1 | 10/2006 | DeVore | |
| 2006/0264772 A1 | 11/2006 | Aljuri et al. | |
| 2006/0276807 A1 | 12/2006 | Keast et al. | |
| 2006/0280772 A1 | 12/2006 | Roschak et al. | |
| 2006/0280773 A1 | 12/2006 | Roschak et al. | |
| 2006/0283462 A1 | 12/2006 | Fields et al. | |
| 2007/0005083 A1 | 1/2007 | Sabanathan et al. | |
| 2007/0027434 A1 | 2/2007 | Pedersen et al. | |
| 2007/0043350 A1 | 2/2007 | Soltesz et al. | |
| 2007/0051372 A1 | 3/2007 | Tanaka | |
| 2007/0055175 A1 | 3/2007 | Caro | |
| 2007/0088300 A1 | 4/2007 | Cline et al. | |
| 2007/0123922 A1 | 5/2007 | Cooper et al. | |
| 2007/0128174 A1 | 6/2007 | Kleinsek et al. | |
| 2007/0142742 A1 | 6/2007 | Aljuri et al. | |
| 2007/0163598 A1 | 7/2007 | Chang et al. | |
| 2007/0185531 A1 | 8/2007 | Rimbaugh et al. | |
| 2007/0186932 A1 | 8/2007 | Wondka et al. | |
| 2007/0186933 A1 | 8/2007 | Domingo et al. | |

FOREIGN PATENT DOCUMENTS

| | | |
|---|---|---|
| EP | 0609950 A1 | 10/1994 |
| RU | 2192185 | 10/2002 |
| WO | WO 88/01879 | 3/1988 |
| WO | WO 90/04982 | 5/1990 |
| WO | WO 99/45990 | 9/1999 |
| WO | WO 99/66975 | 12/1999 |
| WO | WO 00/76577 A1 | 12/2000 |
| WO | WO 01/02042 A1 | 1/2001 |
| WO | WO 01/45568 A1 | 6/2001 |
| WO | WO 02/076279 A2 | 10/2002 |
| WO | WO 02/096325 A1 | 12/2002 |
| WO | WO 03/007821 A1 | 1/2003 |
| WO | WO 03/020338 A2 | 3/2003 |
| WO | WO 03/061480 A1 | 7/2003 |

OTHER PUBLICATIONS

Ball, Jr et al., "Percutaneous Drainage of Chest Abscesses in Children", Radiology 1989; 171: 431-434.
Becker et al., "Lung Volumes before and after Lung Volume Reduction Surgery: Quantitative CT Analysis", Am J Respir Crit Care Med 1998; 157: 1593-1599.
Brenner et al., "Innovative Approaches to Lung Volume Reduction for Emphysema", Chest 2004; 126: 238-248.
Brutinel et al., "A two-year experience with the neodymium-YAG laser in endobronchial obstruction", Chest 1987; 91: 159-165.
Celli et al. "Standards for the diagnosis and treatment of patients with COPD: a summary of the ATS/ERS position paper", European Respiratory Journal 2004; 23; 932-946.
Cetti et al., "Collateral ventilation", Thorax 2006; 61: 371-373.
Chino et al., "Ventilation of Excised Human Lungs Via Spiracles through the Pleura", Thematic Poster Session (Abstract p. A546) Session: 12:45 pm-4:15 pm, Mechanics of the Lung and Respiratory System.
Choong et al., "Feasibility and safety of airway bypass stent placement and influence of topical mitomycin C on stent patency", The Journal of Thoracic and Cardiovascular Surgery 2005; 129: 632-638.
Choong et al., "Transpleural ventilation of explanted human lungs", Thorax 2007; 62: 623-630; originally published online Apr. 5, 2007.
Cope, J. Hallam, "Monaldi Procedure", Presented at the annual meeting of the California Tuberculosis and Health Association and the California Trudeau Society, Mar. 30-Apr. 1, 1950, San Diego; retrieved from California Medicine Dec. 1950; vol. 73, No. 6: 563-564.
Dumon, J. F., "A Dedicated Tracheobronchial Stent", Chest 1990; 97: 328-332.
Eloesser, "An Operation for Tuberculous Empyema", Chest 1935; 1: 8-23.
Fein, Alan M, "Lung Volume Reduction Surgery: Answering the Crucial Questions", Chest 1998; 113: 277-282.
Fernandes et al., "*Airway Hyperresponsiveness: From Molecules to Bedside Invited Review*: Do inflammatory mediators influence the contribution of airway smooth muscle contraction to airway hyperresponsiveness in asthma?", Journal Appl Physiol 2003; 95; 844-853.
Fessler, Henry E., "Collateral Ventilation, the Bane of Bronchoscopic Volume Reduction", Am J Respir Crit Care Med 2005; 171: 423-425.
Frawley et al., "Airway Pressure Release Ventilation: Theory and Practice", AACN Clinical Issues 2001; vol. 12, No. 2: 234-246.
Freitag et al., "Theoretical and experimental basis for the development of a dynamic airway stent", European Respiratory Journal 1994; 7: 2038-2045.
Ghaye et al., "Imaging guided thoracic interventions", European Respiratory Journal 2001; 17: 507-528.
Golding et al., "External drainage of large bullae in severe generalized emphysema", Journal of Thoracic and Cardiovascular Surgery Jun. 1968; vol. 55, No. 6: 891-894.
Goldstraw et al., "The Surgical Treatment of Emphysema: The Brompton Approach", Chest Surgery Clinics of North America Nov. 1995; vol. 5, No. 4: 777-797.
Habashi, Nader M., "Other approaches to open-lung ventilation: Airway pressure release ventilation", Crit Care Med 2005, vol. 33, No. 3 (Suppl): S228-S240.
Harada et al., "Re-expansion of Refractory Atelectasis Using a Bronchofiberscope with a Balloon Cuff", Chest 1983; 84: 725-728.
Head et al., "Intracavitary Suction (Monaldi) in the Treatment of Emphysematous Bullae and Blebs", Journal of Thoracic Surgery Dec. 1949; vol. 18, No. 6: 761-776.
Heimlich, Henry J., "Respiratory Rehabilitation with Transtracheal Oxygen System", Ann Otol Rhinol Laryngol Nov./Dec. 1982; 91: 643-647.
Hogg et al., "Chronic obstructive pulmonary disease c2: Pathology and biochemistry of emphysema", Thorax 2002; 57: 830-834.
Hogg et al., "The Resistance of Collateral Channels in Excised Human Lungs", Journal of Clinical Investigation 1969; 48: 421-431.
Joannette, Albert, "Drainage of Tuberculous Cavities by Aspiration (Monaldi Method)", The Canadian Medical Association Journal Jan. 1941; 46-48.
Korpela et al., "Bioabsorbable Self-reinforced Poly-L-Lactide, Metallic, and Silicone Stents in the Management of Experimental Tracheal Stenosis", Chest 1999; 115: 490-495.
Lausberg et al., "Bronchial Fenestration Improves Expiratory Flow in Emphysematous Human Lungs", Annals of Thoracic Surgery 2003; 75: 393-398.
Lorenzo et al., "Lung Abscesses in Children: Diagnostic and Therapeutic Needle Aspiration", Radiology Oct. 1985; 157: 79-80.
MacArthur et al., "Intracavity suction and drainage in the treatment of emphysematous bullae", Thorax 1977; 32: 668-672.
Macklem, Peter T., "Collateral Ventilation", The New England Journal of Medicine Jan. 5, 1978; 298(1): 49-50.
Matson et al., "Evaluation of Various Surgical Procedures in the Treatment of Pulmonary Tuberculosis", Chest 1946; 12: 40-47.
McCoy, Robert, "Oxygen-Conserving Techniques and Devices", Respiratory Care Jan. 2000, vol. 45, No. 1: 95-100.
Meyers et al., "Chronic obstructive pulmonary disease 10: Bullectomy, lung volume reduction surgery, and transplantation for patients with chronic obstructive pulmonary disease", Thorax 2003; 58: 634-638.
Mineo et al., "Awake Nonresectional Lung Volume Reduction Surgery", Annals of Surgery 2006; 243: 131-136.
Monaldi, V., "Endocavitary Aspiration: Its Practical Application", Tubercle 1947: 223-228.
Monaldi, V., "Endocavitary Aspiration in the Treatment of Lung Abscess", Chest 1956; 29: 193-201.

Monaldi, V., "Endocavitary Aspiration in the Treatment of Pathological Cavities of the Lung", Proceedings of the International Conference on Tuberculosis, Scandinavian Journal of Respiratory Diseases Supplementum 1968; 65: 113-121.

U.S. Department of Health and Human Services; National Institutes of Health National Heart, Lung, and Blood Institute; "Chronic Obstructive Pulmonary Disease", NIH Publication No. 03-5229 Mar. 2003: 1-6.

Parker et al., "Percutaneous small bore catheter drainage in the management of lung abscesses", Chest 1987; 92: 213-218.

Petty, Thomas L., "The history of COPD", International Journal of COPD 2006; 1(1): 3-14.

Polkey, M. J., "Surgical procedures in emphysema: any impact on dynamic hyperinflation?" European Respiratory Review 2006; 15(100): 96-98.

Polkey, M. J., "Bronchoscopic lung volume reduction", European Respiratory Review 2006; 15(100): 99-103.

Rendina et al., "Feasibility and safety of the airway bypass procedure for patients with emphysema", The Journal of Thoracic and Cardiovascular Surgery 2003; 125: 1294-1299.

Rockey, Edward E., "Tube Pneumonostomy for Thoracotomy Reject Crippling Bulbous Emphysema", New York State Journal of Medicine Mar. 1, 1973: 664-671.

Rousseau et al., "Self-expandable Prostheses in the Tracheobronchial Tree", Thoracic Radiology 1993; 188: 199-203.

Russi et al., "Lung volume reduction surgery: what can we learn from the National Emphysema Treatment Trial?" European Respiratory Journal 2003; 22: 571-573.

Saad et al., "Surgical treatment of bullae for Bulbous emphysema: a simple drainage", J. Pneumologia 2000; 26(3): 1-11, retrieved from <http://www.scielo.br/scielo.php?script=arttext&pid=S0102-35862000000300003&Ing=e...> May 2, 2007.

Shah, Pallav, "Surgical and Non-surgical Volume Reduction for COPD", Presented at the Clinical Consensus on COPD, Mar. 2-3, 2007, Novotel London West, 56 pages; see p. 55 of 56.

Shah et al., "Surgical Treatment of Bulbous Emphysema: Experience with the Brompton Technique", Annals of Thoracic Surgery 1994; 58: 1452-1456.

Shim et al., "Percutaneous Drainage of Lung Abscess", Lung 1990; 168: 201-207.

Snell et al., "The Potential for Bronchoscopic Lung Volume Reduction Using Bronchial Prostheses: A Pilot Study", Chest 2003; 124: 1073-1080.

Snell, Gregory I., "Airway Bypass Stenting for Severe Emphysema", retrieved from <http://www.ctsnet.org/sections/thoracic/newtechnology/article-4.html>, Aug. 6, 2007, 4 pages.

Springmeyer, Steven C., "Development of a Bronchial Valve for Treatment of Severe Emphysema", retrieved from <http://www.ctsnet.org/sections/thoracic/newtechnology/article-10.html>, Jul. 16, 2007, 6 pages.

Stewart et al., "Decompression of Giant Bulla in Acute Pneumonia: Surgical Palliation Prior to Definitive Management", Ann Thoracic Surg 2006; 82: 2308-2309.

Sugarmann et al., "Mesh insertion as an aid for pleurodesis", Journal of Cardiovascular Surgery 1996; 37 (Suppl. 1 to No. 6):173-5.

Swallow et al., "Quadriceps strength predicts mortality in patients with moderate to severe chronic obstructive pulmonary disease", Thorax 2007; 62: 115-120.

Symbas et al., "Nontuberculous Pleural Empyema in Adults, The Role of a Modified Eloesser Procedure in Its Management", The Annals of Thoracic Surgery 1971; 12: 69-78.

Takizawa et al., "Computed tomography-guided drainage for large pulmonary bullae", Interactive Cardiovascular and Thoracic Surgery 2004; 3: 283-285.

Terry et al., "Collateral Ventilation in Man", The New England Journal of Medicine 1978; 298(1): 10-15.

Thourani et al., "Twenty-six Years of Experience With the Modified Eloesser Flap", Ann Thorac Surg 2003; 76: 401-406.

Toma et al., "Brave new world for interventional bronchoscopy", Thorax 2005; 60: 180-181.

Ugama et al., "Drainage of Giant Bulla with Balloon Catheter Using Chemical Irritant and Fibrin Glue", Chest 1988; 94(6): 1289-1290.

Vainrub et al., "Percutaneous Drainage of Lung Abscess", American Review of Respiratory Disease 1978; 117: 153-160.

Venn et al., "Intracavity drainage for Bulbous, emphysematous lung disease: experience with the Brompton technique", Thorax 1988; 43: 998-1002.

Wood et al., "A multicenter trial of an intrabronchial valve for treatment of severe emphysema", The Journal of Thoracic and Cardiovascular Surgery 2007; 133: 65-73.

Woolcock et al., "Mechanical factors influencing collateral ventilation in human, dog, and pig lungs", Journal of Applied Physiology 1971; 30: 99-115.

Woodring et al., "Pneumothorax ex vacuo", Chest 1996, 110: 1102-1105.

Yellin et al., "Percutaneous Tube Drainage: The Treatment of Choice for Refractory Lung Abscess", The Annals of Thoracic Surgery 1985; 39: 266-270.

Yim et al., "Minimally invasive thoracic surgery: where do we stand now?" Hong Kong Medical Journal 1995; 1: 115-122.

Yim et al., "Early results of endoscopic lung volume reduction for emphysema", The Journal of Thoracic and Cardiovascular Surgery 2004; 127: 1564-1573.

VARIABLE RESISTANCE PULMONARY VENTILATION BYPASS VALVE

CLAIM OF PRIORITY

This application is a continuation of U.S. patent application Ser. No. 11/332,977 filed on Jan. 17, 2006 which is incorporated herein by reference.

BACKGROUND OF THE INVENTION

1. Field of the Invention

The present invention relates to devices for treating diseased lungs, and more particularly, to a device for controlling the flow of air being vented from predetermined sites in the lung or lungs.

2. Discussion of the Related Art

As a result of studies that date back to the 1930's and particularly studies conducted in the 1960's and early 1970's, it has been determined that long-term continuous oxygen therapy is beneficial in the treatment of hypoxemic patients with chronic obstructive pulmonary disease. In other words, a patient's life and quality of life can be improved by providing a constant supplemental supply of oxygen to the patient's lungs.

However, with the desire to contain medical costs, there is a growing concern that the additional cost of providing continuous oxygen therapy for chronic lung disease will create an excessive increase in the annual cost of oxygen therapy. Thus, it is desirable that oxygen therapy, when provided, be as cost effective as possible.

The standard treatment for patients requiring supplemental oxygen is still to deliver oxygen from an oxygen source by means of a nasal cannula. Such treatment, however, requires a large amount of oxygen, which is wasteful and can cause soreness and irritation to the nose, as well as being potentially aggravating. Other undesirable effects have also been reported. Various other medical approaches, which have been proposed to help reduce the cost of continuous oxygen therapy, have been studied.

Various devices and methods have been devised for performing emergency cricothyroidotomies and for providing a tracheotomy tube so that a patient whose airway is otherwise blocked may continue to breath. Such devices are generally intended only for use with a patient who is not breathing spontaneously and are not suitable for the long term treatment of chronic lung disease. Typically, such devices are installed by puncturing the skin to create a hole into the cricoid membrane of the larynx above the trachea into which a relatively large curved tracheotomy tube is inserted. As previously described, the use of such tubes has been restricted medically to emergency situations where the patient would otherwise suffocate due to the blockage of the airway. Such emergency tracheotomy tubes are not suitable for long term therapy after the airway blockage is removed.

Other devices which have been found satisfactory for emergency or ventilator use are described in U.S. Pat. Nos. 953,922 to Rogers; 2,873,742 to Shelden; 3,384,087 to Brummelkamp; 3,511,243 to Toy; 3,556,103 to Calhoun; 2,991,787 to Shelden, et al; 3,688,773 to Weiss; 3,817,250 to Weiss, et al.; and 3,916,903 to Pozzi.

Although tracheotomy tubes are satisfactory for their intended purpose, they are not intended for chronic usage by outpatients as a means for delivering supplemental oxygen to spontaneously breathing patients with chronic obstructive pulmonary disease. Such tracheotomy tubes are generally designed so as to provide the total air supply to the patient for a relatively short period of time. The tracheotomy tubes are generally of rigid or semi-rigid construction and of caliber ranging from 2.5 mm outside diameter in infants to 15 mm outside diameter in adults. They are normally inserted in an operating room as a surgical procedure or during emergency situations, through the crico-thyroid membrane where the tissue is less vascular and the possibility of bleeding is reduced. These devices are intended to permit passage of air in both directions until normal breathing has been restored by other means.

Another type of tracheotomy tube is disclosed in Jacobs, U.S. Pat. Nos. 3,682,166 and 3,788,326. The catheter described therein is placed over 14 or 16-gauge needle and inserted through the crico-thyroid membrane for supplying air or oxygen and vacuum on an emergency basis to restore the breathing of a non-breathing patient. The air or oxygen is supplied at 30 to 100 psi for inflation and deflation of the patient's lungs. The Jacobs catheter, like the other tracheotomy tubes previously used, is not suitable for long-term outpatient use, and could not easily be adapted to such use.

Due to the limited functionality of tracheotomy tubes, transtracheal catheters have been proposed and used for long term supplemental oxygen therapy. For example the small diameter transtracheal catheter (16 gauge) developed by Dr. Henry J. Heimlich (described in THE ANNALS OF OTOLOGY, RHINOLOGY & LARYNGOLOGY, November-December 1982; Respiratory Rehabilitation with Transtracheal Oxygen System) has been used by the insertion of a relatively large cutting needle (14 gauge) into the trachea at the mid-point between the cricothyroid membrane and the sternal notch. This catheter size can supply oxygen up to about 3 liters per minute at low pressures, such as 2 psi which may be insufficient for patients who require higher flow rates. It does not, however, lend itself to outpatient use and maintenance, such as periodic removal and cleaning, primarily because the connector between the catheter and the oxygen supply hose is adjacent and against the anterior portion of the trachea and cannot be easily seen and manipulated by the patient. Furthermore, the catheter is not provided with positive means to protect against kinking or collapsing which would prevent its effective use on an outpatient basis. Such a feature is not only desirable but necessary for long term outpatient and home care use. Also, because of its structure, i.e. only one exit opening, the oxygen from the catheter is directed straight down the trachea toward the bifurcation between the bronchi. Because of the normal anatomy of the bronchi wherein the left bronchus is at a more acute angle to the trachea than the right bronchus, more of the oxygen from that catheter tends to be directed into the right bronchus rather than being directed or mixed for more equal utilization by both bronchi. Also, as structured, the oxygen can strike the carina, resulting in an undesirable tickling sensation and cough. In addition, in such devices, if a substantial portion of the oxygen is directed against the back wall of the trachea causing erosion of the mucosa in this area which may cause chapping and bleeding. Overall, because of the limited output from the device, it may not operate to supply sufficient supplemental oxygen when the patient is exercising or otherwise quite active or has severe disease.

Diseases associated with chronic obstructive pulmonary disease include chronic bronchitis and emphysema. One aspect of an emphysematous lung is that the communicating flow of air between neighboring air sacs is much more prevalent as compared to healthy lungs. This phenomenon is known as collateral ventilation. Another aspect of an emphysematous lung is that air cannot be expelled from the native airways due to the loss of tissue elastic recoil and radial support of the airways. Essentially, the loss of elastic recoil of the lung tissue contributes to the inability of individuals to exhale completely. The loss of radial support of the airways also allows a collapsing phenomenon to occur during the expiratory phase of breathing. This collapsing phenomenon also intensifies the inability for individuals to exhale completely. As the inability to exhale completely increases, residual volume in the lungs also increases. This then causes the lung to establish in a hyperinflated state where an individual can only take short shallow breaths. Essentially, air is not effectively expelled and stale air accumulates in the lungs. Once the stale air accumulates in the lungs, the individual is deprived of oxygen.

Currently, treatments for chronic obstructive pulmonary disease include bronchodilating drugs, oxygen therapy as described above, and lung volume reduction surgery. Bronchodilating drugs only work on a percentage of patients with chronic obstructive pulmonary disease and generally only provides short-term relief. Oxygen therapy is impractical for the reasons described above, and lung volume reduction surgery is an extremely traumatic procedure that involves removing part of the lung. The long term benefits of lung volume reduction surgery are not fully known.

Accordingly, there exists a need for safely and effectively removing trapped air from a diseased lung or lungs while maintaining control over the flow.

SUMMARY OF THE INVENTION

The present invention overcomes the limitations in treating diseases associated with chronic obstructive pulmonary disorders as briefly described above.

In accordance with one aspect, the present invention comprises a flow control assembly for a collateral ventilation bypass system, comprising at least one device connected, at a predetermined site, to at least one lung for removing trapped gases in the lung and a valve assembly for adjusting the flow of gases from the at least one lung through the at least one device.

The collateral ventilation bypass systems described herein provide a means for eliminating or substantially reducing trapped air in the lung or lungs by facilitating the flow of air via alternate pathways created through the pleura of the lung or lungs. However, by redirecting normal airflow through alternate passageways, the individual may find it somewhat more difficult to carry on certain activities or bodily responses requiring airflow through the native airways, i.e. the trachea. These activities and bodily responses may include speaking, coughing and throat clearing.

The present invention is directed to the incorporation of a flow restrictor device or valve assembly for controlling the flow of air through the conduits of the collateral ventilation bypass system of the present invention. By controlling the airflow through the bypass system, increased air pressure in the lungs may be achieved so that additional air may be forced to flow or travel through the native airways. With this increase in pressure and additional air volume, the individual may be able to speak more easily by forcing more air to flow past the vocal chords, to cough and to clear his or her throat. In addition, an increase in pressure within the lung or lungs may increase gas exchange, thereby making the lung or lungs more efficient. Also, by utilizing a flow restrictor device or valve assembly to restrict or temporarily block the flow of air through the bypass system, the native air passages may be utilized more and thus remain healthy, operational and effective.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
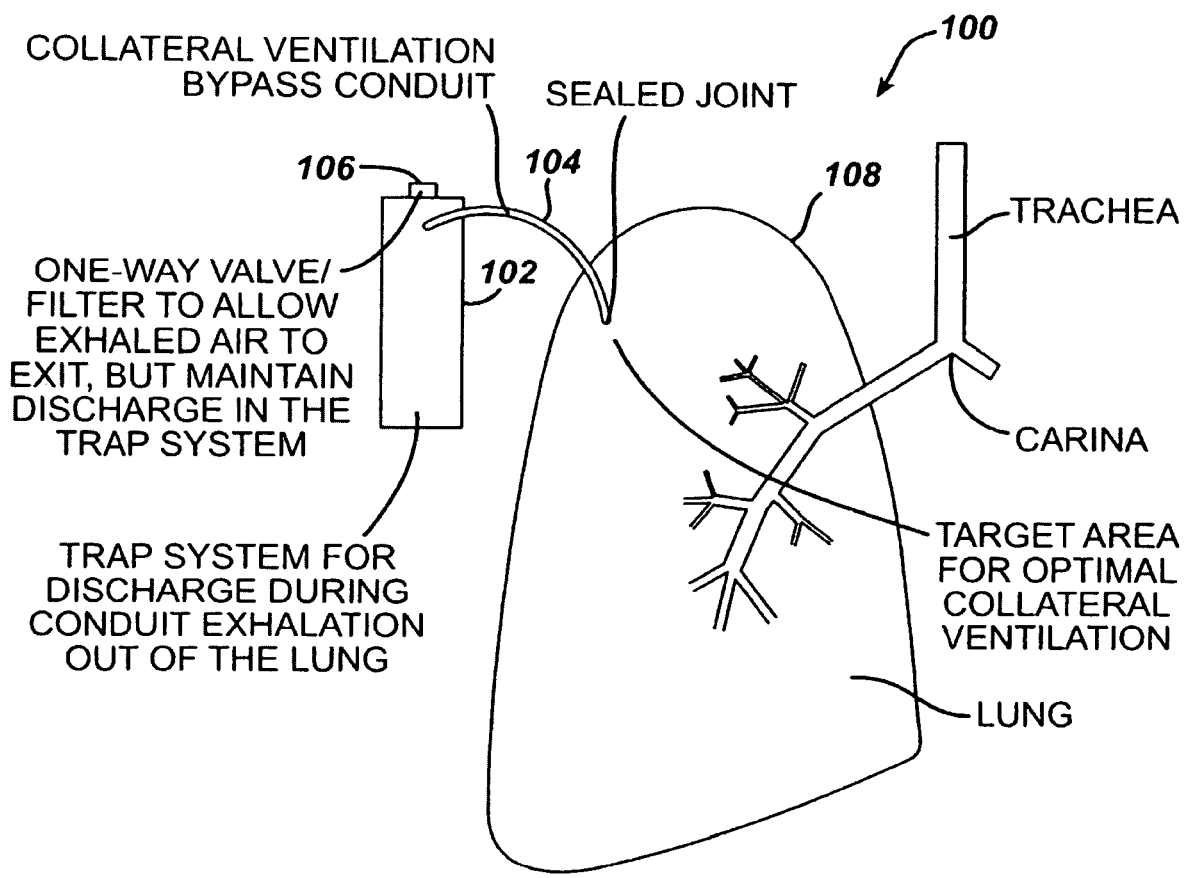
FIG. 1 is a diagrammatic representation of a first exemplary embodiment of a collateral ventilation bypass trap system in accordance with the present invention.

Air typically enters the mammalian body through the nostrils and flows into the nasal cavities. As the air passes through the nostrils and nasal cavities, it is filtered, moistened and raised or lowered to approximately body temperature. The back of the nasal cavities is continuous with the pharynx (throat region); therefore, air may reach the pharynx from the nasal cavities or from the mouth. Accordingly, if equipped, the mammal may breath through its nose or mouth. Generally air from the mouth is not as filtered or temperature regulated as air from the nostrils. The air in the pharynx flows from an opening in the floor of the pharynx and into the larynx (voice box). The epiglottis automatically closes off the larynx during swallowing so that solids and/or liquids enter the esophagus rather than the lower air passageways or airways. From the larynx, the air passes into the trachea, which divides into two branches, referred to as the bronchi. The bronchi are connected to the lungs.

The lungs are large, paired, spongy, elastic organs, which are positioned in the thoracic cavity. The lungs are in contact with the walls of the thoracic cavity. In humans, the right lung comprises three lobes and the left lung comprises two lobes. Lungs are paired in all mammals, but the number of lobes or sections of lungs varies from mammal to mammal. Healthy lungs, as discussed below, have a tremendous surface area for gas/air exchange. Both the left and right lung is covered with a pleural membrane. Essentially, the pleural membrane around each lung forms a continuous sac that encloses the lung. A pleural membrane also forms a lining for the thoracic cavity. The space between the pleural membrane forming the lining of the thoracic cavity and the pleural membranes enclosing the lungs is referred to as the pleural cavity. The pleural cavity comprises a film of fluid that serves as a lubricant between the lungs and the chest wall.

In the lungs, the bronchi branch into a multiplicity of smaller vessels referred to as bronchioles. Typically, there are more than one million bronchioles in each lung. Each bronchiole ends in a cluster of extremely small air sacs referred to as alveoli. An extremely thin, single layer of epithelial cells lining each alveolus wall and an extremely thin, single layer of epithelial cells lining the capillary walls separate the air/gas in the alveolus from the blood. Oxygen molecules in higher concentration pass by simple diffusion through the two thin layers from the alveoli into the blood in the pulmonary capillaries. Simultaneously, carbon dioxide molecules in higher concentration pass by simple diffusion through the two thin layers from the blood in the pulmonary capillaries into the alveoli.

Breathing is a mechanical process involving inspiration and expiration. The thoracic cavity is normally a closed system and air cannot enter or leave the lungs except through the trachea. If the chest wall is somehow compromised and air/gas enters the pleural cavity, the lungs will typically collapse. When the volume of the thoracic cavity is increased by the contraction of the diaphragm, the volume of the lungs is also increased. As the volume of the lungs increase, the pressure of the air in the lungs falls slightly below the pressure of the air external to the body (ambient air pressure). Accordingly, as a result of this slight pressure differential, external or ambient air flows through the respiratory passageways described above and fills the lungs until the pressure equalizes. This process is inspiration. When the diaphragm is relaxed, the volume of the thoracic cavity decreases, which in turn decreases the volume of the lungs. As the volume of the lungs decrease, the pressure of the air in the lungs rises slightly above the pressure of the air external to the body. Accordingly, as a result of this slight pressure differential, the air in the alveoli is expelled through the respiratory passageways until the pressure equalizes. This process is expiration.

Continued insult to the respiratory system may result in various diseases, for example, chronic obstructive pulmonary disease. Chronic obstructive pulmonary disease is a persistent obstruction of the airways caused by chronic bronchitis and pulmonary emphysema. In the United States alone, approximately fourteen million people suffer from some form of chronic obstructive pulmonary disease and it is in the top ten leading causes of death.

Chronic bronchitis and acute bronchitis share certain similar characteristics; however, they are distinct diseases. Both chronic and acute bronchitis involve inflammation and constriction of the bronchial tubes and the bronchioles; however, acute bronchitis is generally associated with a viral and/or bacterial infection and its duration is typically much shorter than chronic bronchitis. In chronic bronchitis, the bronchial tubes secrete too much mucus as part of the body's defensive mechanisms to inhaled foreign substances. Mucus membranes comprising ciliated cells (hair like structures) line the trachea and bronchi. The ciliated cells or cilia continuously push or sweep the mucus secreted from the mucus membranes in a direction away from the lungs and into the pharynx where it is periodically swallowed. This sweeping action of the cilia functions to keep foreign matter from reaching the lungs. Foreign matter that is not filtered by the nose and larynx, as described above, becomes trapped in the mucus and is propelled by the cilia into the pharynx. When too much mucus is secreted, the ciliated cells may become damaged, leading to a decrease in the efficiency of the cilia to sweep the bronchial tubes and trachea of the mucus containing the foreign matter. This in turn causes the bronchioles to become constricted and inflamed and the individual becomes short of breath. In addition, the individual will develop a chronic cough as a means of attempting to clear the airways of excess mucus.

Individuals who suffer from chronic bronchitis may develop pulmonary emphysema. Pulmonary emphysema is a disease in which the alveoli walls, which are normally fairly rigid structures, are destroyed. The destruction of the alveoli walls is irreversible. Pulmonary emphysema may be caused by a number of factors, including chronic bronchitis, long term exposure to inhaled irritants, e.g. air pollution, which damage the cilia, enzyme deficiencies and other pathological conditions. In pulmonary emphysema, the alveoli of the lungs lose their elasticity, and eventually the walls between adjacent alveoli are destroyed. Accordingly, as more and more alveoli walls are lost, the air exchange (oxygen and carbon dioxide) surface area of the lungs is reduced until air exchange becomes seriously impaired. The combination of mucus hypersecretion (described above) and dynamic airway compression are mechanisms of airflow limitation in chronic obstructive pulmonary disease. Dynamic airway compression results from the loss of tethering forces exerted on the airway due to the reduction in lung tissue elasticity. In other words, the breakdown of lung tissue leads to the reduced ability of the lungs to recoil and the loss of radial support of the airways. Consequently, the loss of elastic recoil of the lung tissue contributes to the inability of individuals to exhale completely. The loss of radial support of the airways also allows a collapsing phenomenon to occur during the expiratory phase of breathing. This collapsing phenomenon also intensifies the inability for individuals to exhale completely. As the inability to exhale completely increases, residual volume in the lungs also increases. This then causes the lung to establish in a hyperinflated state where an individual can only take short shallow breaths. Essentially, air is not effectively expelled and stale air accumulates in the lungs. Once the stale air accumulates in the lungs, the individual is deprived of oxygen. There is no cure for pulmonary emphysema, only various treatments, including exercise, drug therapy, such as bronchodilating agents, lung volume reduction surgery and long term oxygen therapy.

In emphysema, alveoli walls are destroyed, thereby causing a decrease in air exchange surface area. As more alveoli walls are destroyed, collateral ventilation resistance is lowered. In other words, pulmonary emphysema causes an increase in collateral ventilation and to a certain extent, chronic bronchitis also causes an increase in collateral ventilation. Essentially, in an emphysematous lung, the communicating flow of air between neighboring air sacs (alveoli), known as collateral ventilation, is much more prevalent as compared to a normal lung. Since air cannot be expelled from the native airways due to the loss of tissue elastic recoil and radial support of the airways (dynamic collapse during exhalation), the increase in collateral ventilation does not significantly assist an individual in breathing. The individual develops dsypnea. Accordingly, if it can be determined where collateral ventilation is occurring, then the diseased lung tissue may be directly treated. Various methods may be utilized to determine the diseased tissue locations, for example, computerized axial tomography or CAT scans, magnetic resonance imaging or MRI, positron emission tomograph or PET, and/or standard X-ray imaging.

As set forth above, emphysema is distinguished as irreversible damage to lung tissue. The breakdown of lung tissue leads to the reduced ability for the lungs to recoil. The tissue breakdown also leads to the loss of radial support of the native airways. Consequently, the loss of elastic recoil of the lung tissue contributes to the inability for individuals with emphysema to exhale completely. The loss of radial support of the native airways also allows a collapsing phenomenon to occur during the expiratory phase of breathing. This collapsing phenomenon also intensifies the inability for individuals to exhale completely. As the inability to exhale increases, residual volume in the lungs also increases. This then causes the lung to establish in a hyperinflated state wherein an individual can only take short shallow breaths.

The collateral ventilation bypass trap system of the present invention utilizes the above-described collateral ventilation phenomenon to increase the expiratory flow from a diseased lung or lungs, thereby treating another aspect of chronic obstructive pulmonary disease. Essentially, the most collaterally ventilated area of the lung or lungs is determined utilizing the scanning techniques described above. Once this area or areas are located, a conduit or conduits are positioned in a passage or passages that access the outer pleural layer of the diseased lung or lungs. The conduit or conduits utilize the collateral ventilation of the lung or lungs and allows the entrapped air to bypass the native airways and be expelled to a containment system outside of the body.

FIG. 1 illustrates a first exemplary collateral ventilation bypass trap system 100. The system 100 comprises a trap 102, an air carrying conduit 104 and a filter/one-way valve 106. The air carrying conduit 104 creates a fluid communication link between an individual's lung 108 and the trap 102 through the filter/one-way valve 106. It is important to note that although a single conduit 104 is illustrated, multiple conduits may be utilized in each lung 108 if it is determined that there is more than one area of high collateral ventilation.

The trap 102 may comprise any suitable device for collecting discharge from the individual's lung or lungs 108. Essentially, the trap 102 is simply a containment vessel for temporarily storing discharge from the lungs, for example, mucous and other fluids that may accumulate in the lungs. The trap 102 may comprise any suitable shape and may be formed from any suitable metallic or non-metallic materials. Preferably, the trap 102 should be formed from a lightweight, non-corrosive material. In addition, the trap 102 should be designed in such a manner as to allow for effective and efficient cleaning. In one exemplary embodiment, the trap 102 may comprise disposable liners that may be removed when the trap 102 is full. The trap 102 may be formed from a transparent material or comprise an indicator window so that it may be easily determined when the trap 102 should be emptied or cleaned. A lightweight trap 102 increases the patient's mobility.

The filter/one-way valve 106 may be attached to the trap 102 by any suitable means, including threaded fittings or compression type fittings commonly utilized in compressor connections. The filter/one-way valve 106 serves a number of functions. The filter/one-way valve 106 allows the air from the individual's lung or lungs 108 to exit the trap 102 while maintaining the fluid discharge and solid particulate matter in the trap 102. This filter/one-way valve 106 would essentially maintain the pressure in the trap 102 below that of the pressure inside the individual's lung or lungs 108 so that the flow of air from the lungs 108 to the trap 102 is maintained in this one direction. The filter portion of the filter/one-way valve 106 may be designed to capture particulate matter of a particular size which is suspended in the air, but allows the clean air to pass therethrough and be vented to the ambient environment. The filter portion may also be designed in such a manner as to reduce the moisture content of the exhaled air.

The air carrying conduit 104 connects the trap 102 to the lung or lungs 108 of the patient through the filter/one-way valve 106. The air carrying conduit 104 may comprise any suitable biocompatible tubing having a resistance to the gases contained in air. The air carrying conduit 104 comprises tubing having an inside diameter in the range from about 1/16 inch to about 1/2 inch, and more preferably from about 1/8 inch to about 1/4 inch. The filter/one-way valve 106 may comprise any suitable valve which allows air to flow from the lung or lungs 108 through the air carrying conduit 104, but not from the trap 102 back to the lungs 108. For example, a simple check valve may be utilized. The air carrying conduit 104 may be connected to the filter/one-way valve 106 by any suitable means. Preferably, a quick release mechanism is utilized so that the trap may be easily removed for maintenance.

As illustrated in FIG. 1, the air carrying conduit 104 passes through the lung 108 at the site determined to have the highest degree of collateral ventilation. If more than one site is determined, multiple air carrying conduits 104 may be utilized. The connection of multiple air carrying conduits 104 to the filter/one-way valve 106 may be accomplished by any suitable means, including an octopus device similar to that utilized in scuba diving regulators.

The air carrying conduit 104 is preferably able to withstand and resist collapsing once in place. Since air will travel through the conduit 104, if the conduit is crushed and unable to recover, the effectiveness of the system is diminished. Accordingly, a crush recoverable material may be incorporated into the air carrying conduit 104 in order to make it crush recoverable. Any number of suitable materials may be utilized. For example, Nitinol incorporated into the conduit 104 will give the conduit collapse resistance and collapse recovery properties. In this type of exemplary embodiment, nitinol wire may be embedded in the conduit 104 and treated or programmed to maintain an expanded diameter. In other words, the conduit 104 may comprise a polymeric coating over a suitably arranged nitinol base structure. The polymeric coating or cover layer may be formed from any available biocompatible polymeric materials, including polytetrafleurethelene, silicone and polyurethanes.

Expandable features at the end of the conduit 104 may be used to aid in maintaining contact and sealing the conduit 104 to the lung pleura. Nitinol incorporated into the conduit 104 will provide the ability to deliver the conduit 104 in a compressed state and then deployed in an expanded state to secure it in place. Shoulders at the end of the conduit may also provide a mechanical stop for insertion and an area for an adhesive/sealant to join as described in detail subsequently.

In order for the exemplary collateral ventilation bypass trap system 100 to function, an airtight seal is preferably maintained where the air carrying conduit 104 passes through the thoracic cavity and lungs 108. This seal is maintained in order to sustain the inflation/functionality of the lungs. If the seal is breached, air may enter the cavity and cause the lungs to collapse. One exemplary method for creating the seal comprises forming adhesions between the visceral pleura of the lung and the inner wall of the thoracic cavity. This may be achieved using either chemical methods, including irritants such as Doxycycline and/or Bleomycin, surgical methods, including pleurectomy or thorascopic talc pleurodesis, or radiotherapy methods, including radioactive gold or external radiation. All of these methods are known in the relevant art for creating pleurodesis. In another alternate exemplary embodiment, a sealed joint between the air carrying conduit 104 and the outer pleural layer includes using various glues to help with the adhesion/sealing of the air carrying conduit 104. Currently, Focal Inc. markets a sealant available under the tradename Focal/Seal-L which is indicated for use on a lung for sealing purposes. Focal/Seal-L is activated by light in order to cure the sealant. Another seal available under the tradename Thorex, which is manufactured by Surgical Sealants Inc., is currently conducting a clinical trial for lung sealing indications. Thorex is a two-part sealant that has a set curing time after the two parts are mixed.

The creation of the opening in the chest cavity may be accomplished in a number of ways. For example, the procedure may be accomplished using an open chest procedure, aternotomy or thoracotomy. Alternately, the procedure may be accomplished using a laproscopic technique, which is less invasive. Regardless of the procedure utilized, the seal should be established while the lung is at least partially inflated in order to maintain a solid adhesive surface. The opening may then be made after the joint has been adequately created between the conduit component and the lung pleural surface. The opening should be adequate in cross-sectional area in order to provide sufficient decompression of the hyperinflated lung. This opening, as stated above, may be created using a number of different techniques such as cutting, piercing, dilating, blunt dissection, radio frequency energy, ultrasonic energy, microwave energy, or cryoblative energy.

Figure 2:
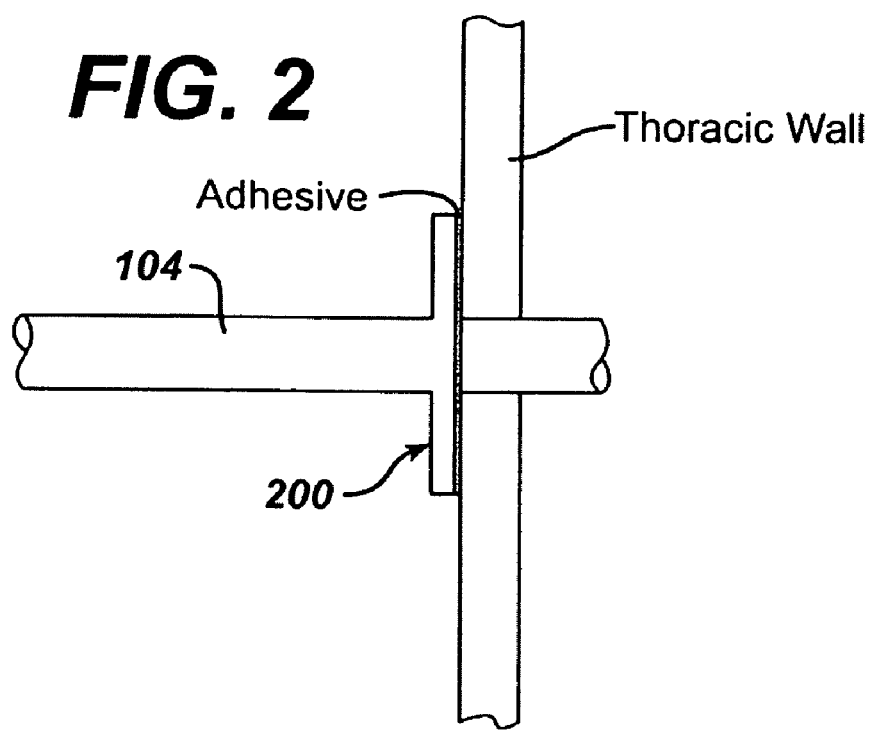
FIG. 2 is a diagrammatic representation of a first exemplary embodiment of a sealing device utilized in conjunction with the long term oxygen therapy system of the present invention.

The air carrying conduit 104 may be sealed to the skin by any suitable means. Similarly to ostomy pouches or bags, the air carrying conduit 104 may be sealed to the skin at the site of the ventilation bypass. In one exemplary embodiment as illustrated in FIG. 2, the air carrying conduit 104 may be sealed to the skin of the thoracic wall utilizing an adhesive. As illustrated, the air carrying conduit 104 comprises a flange 200 having a biocompatible adhesive coating on the skin contacting surface. The biocompatible adhesive would provide a fluid tight seal between the flange 200 and the skin or epidermis of the thoracic wall. In a preferred embodiment, the biocompatible adhesive provides a temporary fluid tight seal such that the air carrying conduit 104 may be disconnected from the ventilation bypass site. This would allow for the site to be cleaned and for the collateral ventilation bypass system 100 to undergo periodic maintenance.

Figure 3:
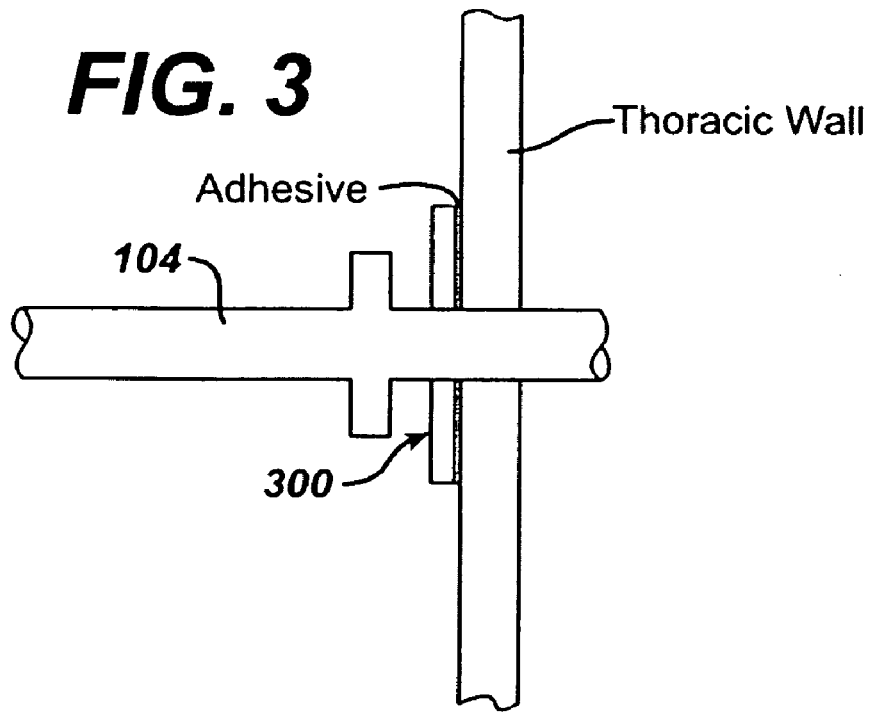
FIG. 3 is a diagrammatic representation of a second exemplary embodiment of a sealing device utilized in conjunction with the long term oxygen therapy system of the present invention.

FIG. 3 illustrates another exemplary embodiment for sealing the air carrying conduit 104 to the skin of the thoracic wall at the site of the ventilation bypass. In this exemplary embodiment, a coupling plate 300 is sealed to the skin at the site of the ventilation bypass by a biocompatible adhesive coating or any other suitable means. The air carrying conduit 104 is then connected to the coupling plate 300 by any suitable means, including threaded couplings and locking rings. The exemplary embodiment also allows for cleaning of the site and maintenance of the system 100.

Figure 4:
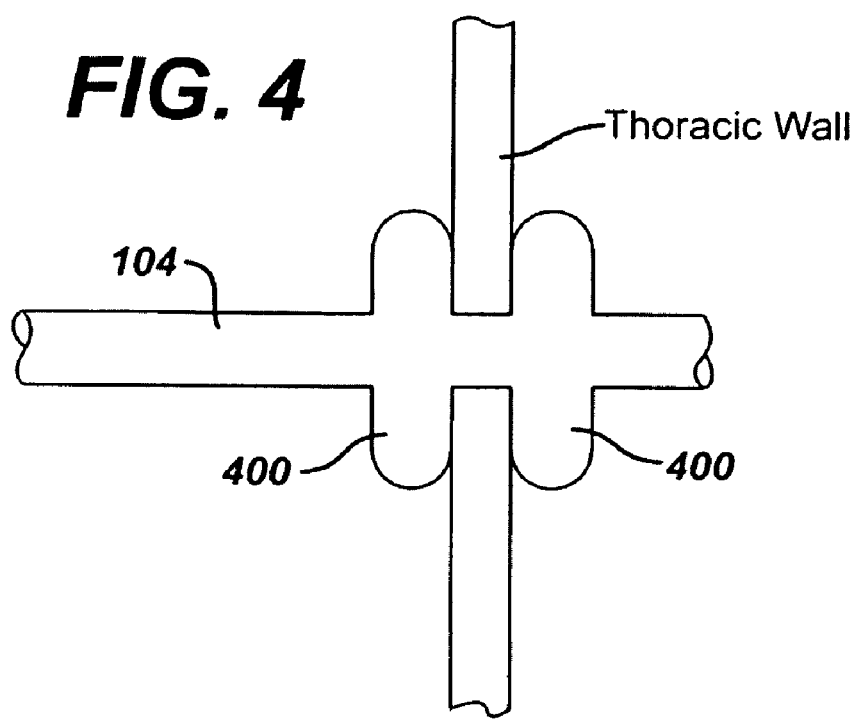
FIG. 4 is a diagrammatic representation of a third exemplary embodiment of a sealing device utilized in conjunction with the long term oxygen therapy system of the present invention.

FIG. 4 illustrates yet another exemplary embodiment for sealing the air carrying conduit 104 to the skin of the thoracic wall at the site of the ventilation bypass. In this exemplary embodiment, balloon flanges 400 may be utilized to create the seal. The balloon flanges 400 may be attached to the air carrying conduit 104 such that in the deflated state, the air carrying conduit 104 and one of the balloon flanges passes through the ventilation bypass anastomosis. The balloon flanges 400 are spaced apart a sufficient distance such that the balloon flanges remain on opposite sides of the thoracic wall. When inflated, the balloons expand and form a fluid tight seal by sandwiching the thoracic wall. Once again, this exemplary embodiment allows for easy removal of the air carrying conduit 104.

Figure 5:
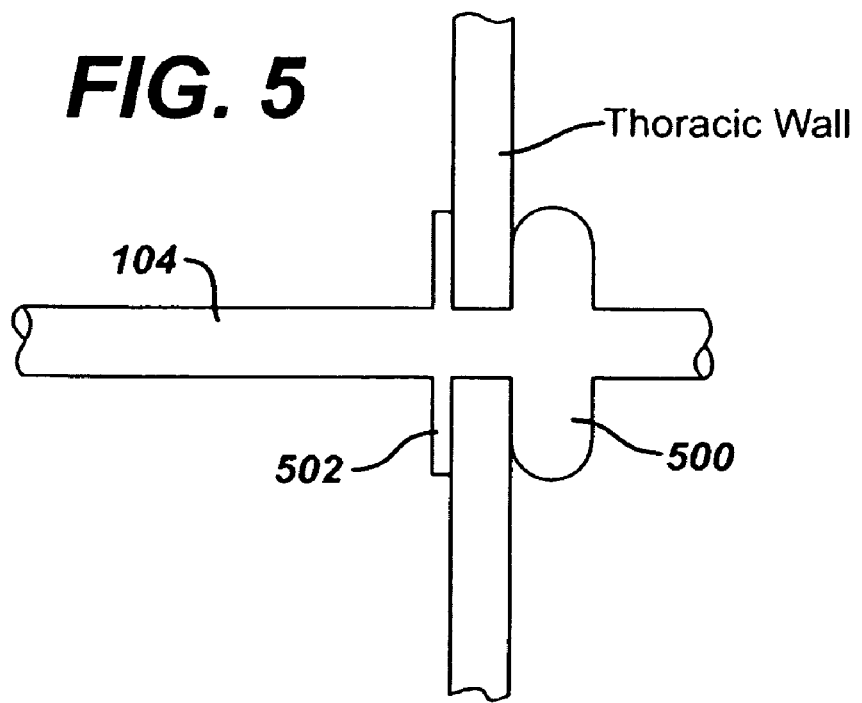
FIG. 5 is a diagrammatic representation of a fourth exemplary embodiment of a sealing device utilized in conjunction with the long term oxygen therapy system of the present invention.

FIG. 5 illustrates yet another exemplary embodiment for sealing the air carrying conduit 104 to the skin of the thoracic wall at the site of the ventilation bypass. In this exemplary embodiment, a single balloon flange 500 is utilized in combination with a fixed flange 502. The balloon flange 500 is connected to the air carrying conduit 104 in the same manner as described above. In this exemplary embodiment, the balloon flange 500, when inflated, forms the fluid tight seal. The fixed flange 502, which is maintained against the skin of the thoracic wall, provides the structural support against which the balloon exerts pressure to form the seal.

In operation, when an individual exhales, the pressure in the lungs is greater than the pressure in the trap 102. Accordingly, the air in the highly collateralized areas of the lung will travel through the air carrying conduit 104 to the trap 102. This operation will allow the individual to more easily and completely exhale.

Figure 6:
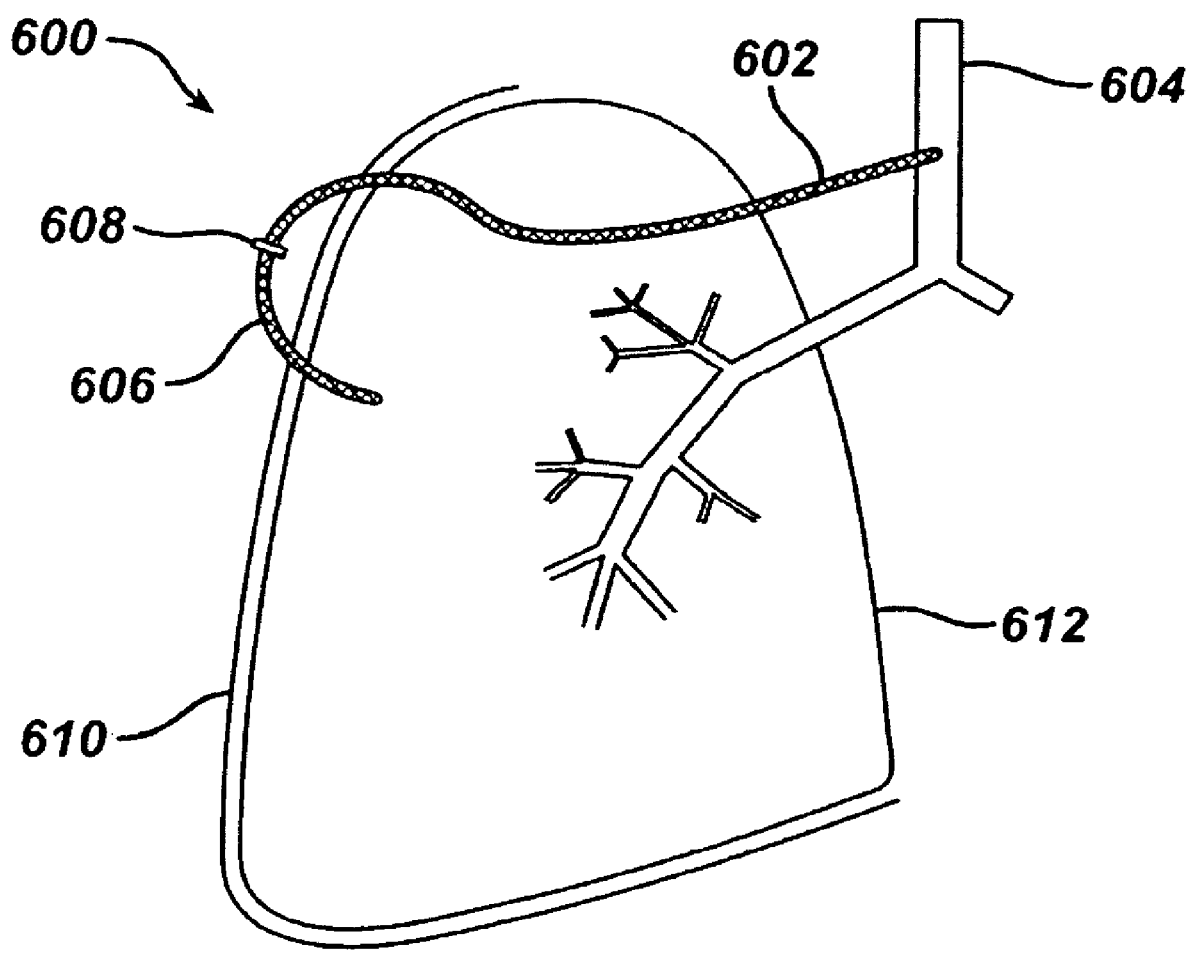
FIG. 6 is a diagrammatic representation of a second exemplary embodiment of a collateral ventilation bypass system in accordance with the present invention.

FIG. 6 illustrates another exemplary collateral ventilation bypass system 600. In this exemplary embodiment, the trachea is utilized to remove trapped air rather than the native airways. As illustrated, a first conduit 602 extends from the patient's trachea 604, or other proximal airways, including the bronchus, to a position external of the patient's body. A second conduit 606 is connected to the first conduit 602 via a fitting 608 and passes through the thoracic wall 610 and passes through the lung 612 at the site determined to have the highest degree of collateral ventilation. If more than one site is determined to have a high degree of collateral ventilation, multiple conduits may be utilized. In operation, when the patient exhales, the pressure in the lungs is greater than the pressure in the trachea 604; accordingly, the air in the highly collateralized areas of the lung will travel through the first and second conduits 602, 606 to the trachea 604 and out of the patient's nose and mouth with the normally exhaled air.

The first and second conduits 602, 606 may comprise any suitable biocompatible tubing having a resistance to the various gases and other constituents contained in inhaled and exhaled air. As in previously described embodiments, the first and second conduits 602, 606 comprise tubing having an inside diameter in the range from about 1/16 inch to about 1/2 inch, and more preferably from about 1/8 inch to about 1/4 inch.

The connection of the first conduit 602 to the trachea 604 may comprise any suitable airtight seal. For example, a fluid communication link between the trachea 604 and the first conduit 602 may be established in a manner identical to that established for a tracheotomy. In addition, as stated above, in order for the collateral ventilation bypass system 600 to function, an airtight seal is preferably maintained where the second conduit 606 passes through the thoracic wall 610 and into the lungs 612. An exemplary method for creating this airtight seal comprises forming adhesions between the visceral pleura of the lung and the parietal pleura. This may be achieved using either chemical methods, including irritants, surgical methods, including pleurectomy or thorascopic talc pleurodesis, or radiotherapy methods, including radioactive gold or external radiation as is described in detail above.

The conduits 602, 606 may be sealed to the skin at the sites by any known methods, including those described above with respect to FIGS. 2 through 5. The connection of the extrathoracic component, conduit 606, may comprise a drug, chemical, agent, or other means for preventing or substantially reducing the risk of infection.

The fitting 608 connecting the first and second conduits 602, 606 may comprise any suitable device for creating an airtight seal. The fitting 608 may comprise any type of threaded or non-threaded union, compression fittings similar to compressor type fittings or any other suitable device for establishing an airtight seal and providing for quick release between the two ends of the fitting 608. This type of design would allow easy access for periodic maintenance of the system 600, for example, cleaning the conduits 602, 606. Since the fitting 608 is external to the body, access to the inner body component of the system 600 would be easier. Essentially, access of the system 600 from outside the body would allow for maintenance and diagnosis/observation of the system 600 without subjecting the patient to additional stress and risk. It would also be less time consuming for the doctor.

Figure 7:
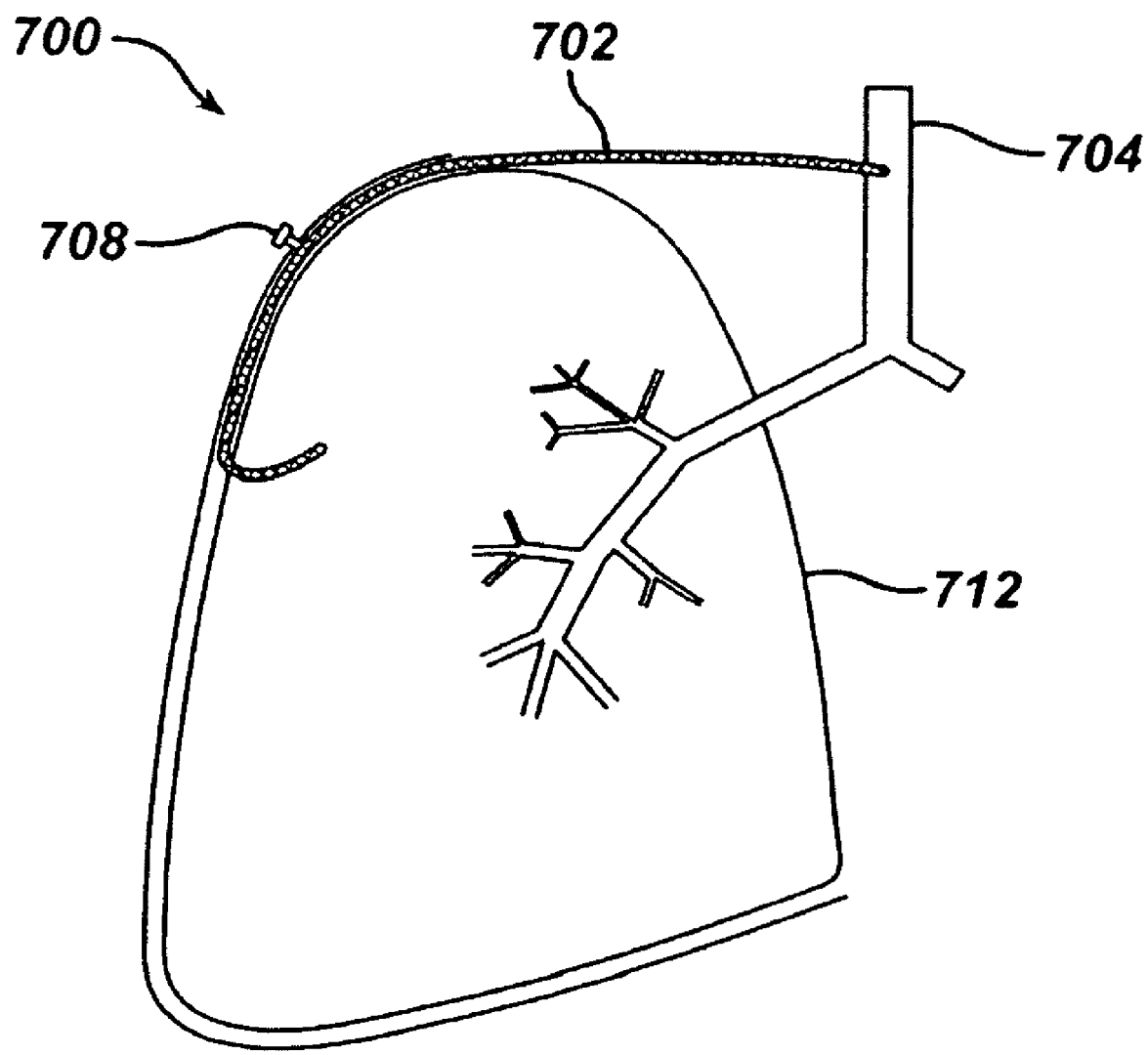
FIG. 7 is a diagrammatic representation of a third exemplary embodiment of a collateral ventilation bypass system in accordance with the present invention.

FIG. 7 illustrates an alternate exemplary embodiment of the exemplary collateral ventilation bypass system 600 described above. In this exemplary embodiment, the system 700 comprises an externally positioned access port 708. As illustrated, a conduit 702 extends from the patient's trachea 704, or other proximal airways, including the bronchus, through a suitable passageway internal to the patient's body and then passes through the lung 712 at the site determined to have the highest degree of collateral ventilation. As set forth above, if more than one site is determined to have a high degree of collateral ventilation, multiple conduits may be utilized. At the desired location within the body, the access port 708 may be placed in-line with the conduit 702 such that at least a portion of the access port 708 is accessible outside of the body. Essentially, the access port 708 should allow the patient or a doctor to open the port and access the system 700 within the patient's body for maintenance and diagnosis/observation of the system 700 as described above.

The access port 708 may comprise any suitable device for providing an airtight seal when closed and easy access to the conduit 702 when open. The access port 708 may comprise various valve arrangements and connectors for connecting other components which may be utilized for various functions. For example, oxygen may be supplied directly to the patient's lungs 712 if needed. In this instance, a valve may be needed to prevent the oxygen from bypassing the lungs 712 and go straight to the trachea 704.

All the remaining components may be the same as described above. In addition, all seals may be accomplished as described above.

Figure 8:
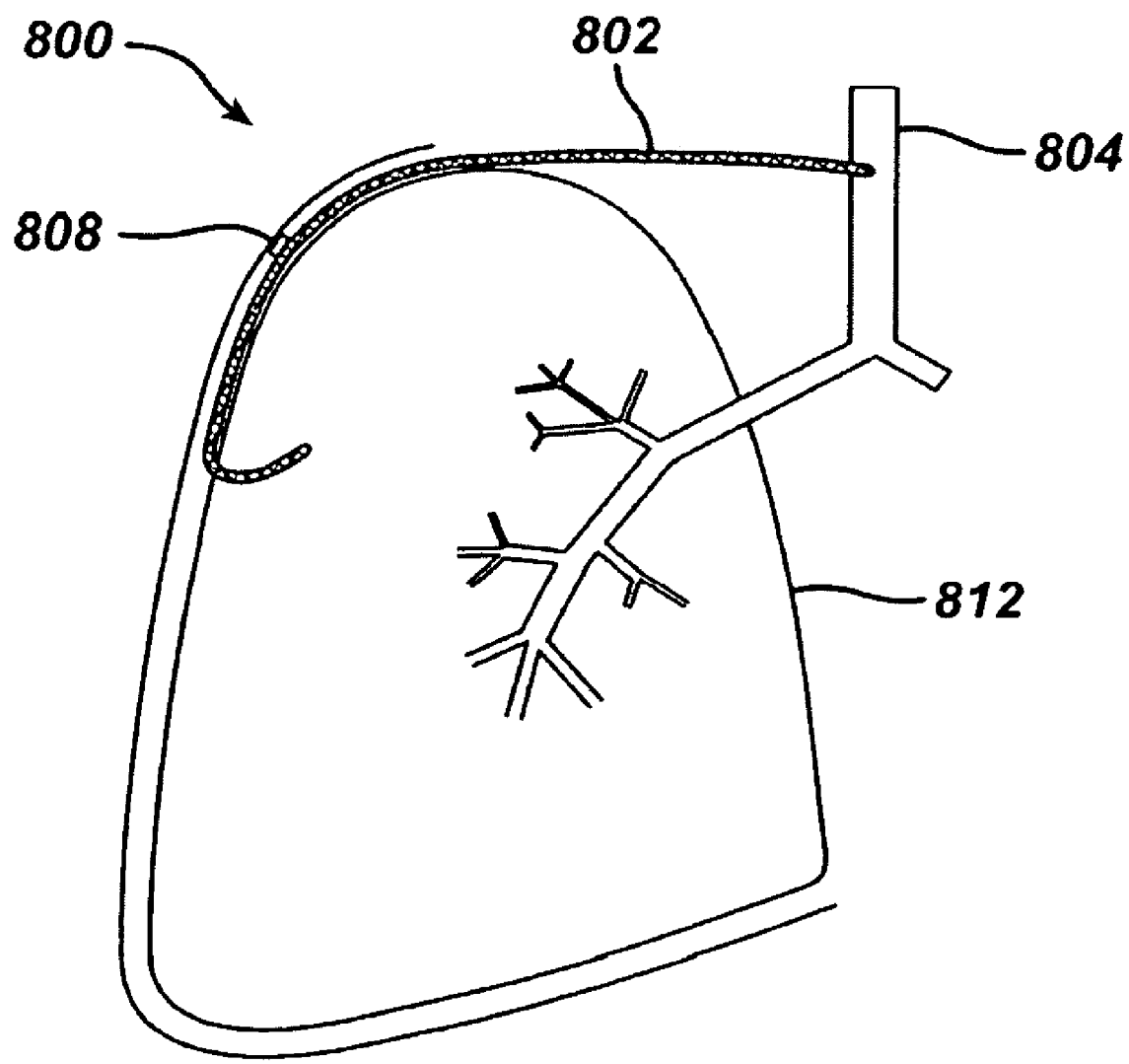
FIG. 8 is a diagrammatic representation of a fourth exemplary embodiment of a collateral ventilation bypass system in accordance with the present invention.

In yet another alternate exemplary embodiment, the extrathoracic access port 708, illustrated in FIG. 7, may be positioned just under the skin so that it is accessible percutaneously. Essentially, the access port would not truly be extrathoracic, but rather just located under the skin and accessible extrathoracically. In this exemplary embodiment access would not be as easily accessible; however, the access point would remain more discrete than the previously described exemplary embodiments. FIG. 8 illustrates this exemplary embodiment.

As illustrated in FIG. 8, the collateral ventilation bypass system 800 comprises a conduit 802 that extends from the patient's trachea 804, or other proximal airways, including the bronchus, through a suitable passageway internal to the patient's body and then passes through the lung 812 at the site determined to have the highest degree of collateral ventilation. As set forth above, if more than one site is determined to have a high degree of collateral ventilation, multiple conduits may be utilized. At the desired location within the body, an internal access port 808 may be placed in-line with the conduit 802. The access port 808 may comprise any suitable device that allows access via percutaneous means. All remaining components may be the same as described above. In addition, all seals may be accomplished as described above.

It is important to note that in each of the above-described exemplary embodiments, additional components may be added that function to prevent flow from the trachea end of the conduit to the lung. For example, one or more valves may be incorporated throughout the systems to prevent mucus and other substances from entering or re-entering the lung. The main function of the system is to allow exhalation. In theory, patients with emphysema have increased resistance to expiration and not inhalation. Any suitable valves may be utilized, for example, one-way check valves.

Figure 9:
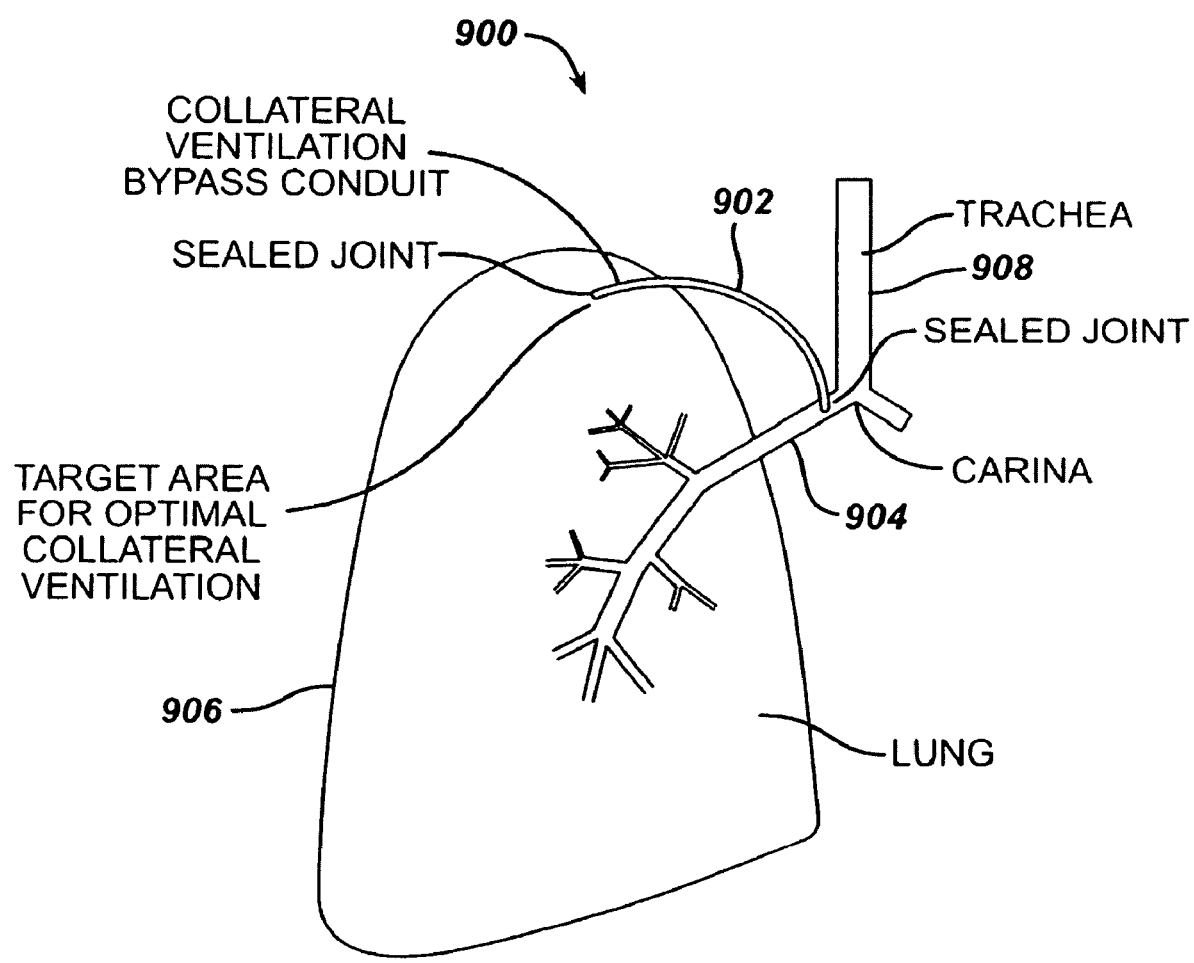
FIG. 9 is a diagrammatic representation of an exemplary embodiment of an intra-thoracic collateral ventilation bypass system in accordance with the present invention.

FIG. 9 illustrates yet another alternate exemplary collateral ventilation bypass system 900. In this exemplary embodiment, like the exemplary embodiments illustrated in FIGS. 6-8, the trachea or other proximal airways, including the bronchus, is utilized to remove air trapped in the lung or lungs. As illustrated, a conduit 902 extends from the patient's bronchus 904 and passes directly into the lung 906 at the site determined to have the highest degree of collateral ventilation. If more than one site is determined to have a high degree of collateral ventilation, multiple conduits may be utilized. In operation, when the patient exhales, the pressure in the lungs is greater than the pressure in the bronchus 904; accordingly, the air in the highly collateralized area or areas of the lung will travel through the conduit 902 to the bronchus 904, into the trachea 908 and out of the patient's nose and mouth, not shown, with the normally exhaled air.

The conduit 902 in this exemplary embodiment does not leave the patient's body. The conduit 902 may comprise any suitable biocompatible tubing having a resistance to the various gases and other constituents contained in inhaled and exhaled air. As in previously described exemplary embodiments, the conduit 902 comprises tubing having an inside diameter in the range from about $\frac{1}{16}$ inch to about $\frac{1}{2}$ inch, and more preferably in the range from about $\frac{1}{8}$ inch to about $\frac{1}{4}$ inch. In addition, the conduit 902 may comprise all of the characteristics described above.

The conduit 902 may also comprise modified ends. For example, expandable features at each end may be utilized to maintain contact and sealing between the conduit 902 and/or the bronchus 904, the trachea 908, and the lung 906 pleura. Once again, nitinol or other similar property materials may be incorporated into the conduit 902 and thus provide the conduit 902 to be delivered in a smaller diameter compressed state and then deployed in a larger diameter expanded state to help secure it in place. Alternately, shoulders at each end of the conduit 902 may also provide a mechanical stop for insertion and an area for an adhesive/sealant to join.

The conduit 902 may be introduced into the body of the patient in a number of ways, including those described herein. In one exemplary embodiment, the conduit 902 may be introduced utilizing an open-chest procedure, for example, a sternotomy or thoracotomy. In an alternate exemplary embodiment, the conduit 902 may be introduced utilizing a laproscopic technique to make the procedure less invasive. It is important to note that the conduit 902 may be incorporated into the opening creating device. If the conduit 902 is incorporated with the opening creating device, the conduit 902 may be inserted and established in the same step as the opening creation.

As stated in the above-described exemplary embodiments, in order for the collateral ventilation bypass system 900 to function, an airtight seal is preferably made between the conduit 902 and the outer pleural layer of the lung 906. This seal is maintained in order to sustain the inflation/functionality of the lungs. If the seal is breached, air can enter the pleural space and cause the lungs to collapse. One method for creating the seal involves pleuroderis or forming adhesions between the visceral pleura of the lung and the inner wall of the thoracic cavity as briefly described above and in more detail subsequently. In another alternate exemplary embodiment, a sealed joint between the conduit 902 and the outer pleural layer includes using various glues to help with the adhesion/sealing of the conduit 902 as described above. Regardless of the procedure utilized, the seal should be established while the lung is at least partially inflated in order to maintain a solid adhesive surface. The opening may then be made after the joint has been adequately created between the conduit 902 and the lung pleural surface. The opening should be adequate in cross-sectional area in order to provide sufficient decompression of the hyperinflated lung.

The connection of the conduit 902 to the trachea or bronchus 904 should also be an airtight seal. For example, fluid communication between the bronchus 904 and the conduit 902 may be established in a manner identical to that established for a tracheotomy.

The conduit 902 may be positioned at any suitable location within the patient's body. Preferably, the conduit 902 is positioned such that it will not affect the patient's ability to function normally.

It is important to note that in the above-described exemplary embodiment, additional components may be added that function to prevent flow from the bronchus to the lung. For example, one or more valves or filters may be incorporated into the conduit to prevent mucus and other substances from entering or re-entering the lung. The main function of the collateral ventilation bypass system is to allow exhalation. In theory, patients with emphysema have increased resistance to expiration and not inspiration. Any suitable valves may be utilized, for example, one-way check valves.

In accordance with another exemplary embodiment, the collateral ventilation bypass systems of the present invention may comprise one or more retention devices to prevent or substantially inhibit the migration of system components, such as conduits, into and out of the lungs and trachea. Although the retention devices described herein may be utilized with any of the collateral ventilation bypass systems described herein or for any system in which elements are preferably held in position, for ease of explanation they will be described with respect to the exemplary embodiment illustrated in FIG. 1.

Essentially, if a system having one or more components is positioned so that it accesses the lung or lungs through the thoracic wall, devices may be needed to be incorporated into the design in order to prevent the components from migrating into or out of fixed positions within the lungs. Retention devices could include embodiments both in the lung tissue and outside the thoracic wall, for example, on the skin. The retention device may only be required for a predetermined period of time or as a permanent implant. If the retention device is utilized as a temporary measure, it may be used after initial implantation to allow a tract to form and/or heal around the device. Once a tract is formed, any subsequent retention devices may only require an element on the skin of the patient as opposed to an additional element in the lung or lungs. However, similar to gastrostomy procedures, a device may require a chronic internal retention feature.

Figure 10:
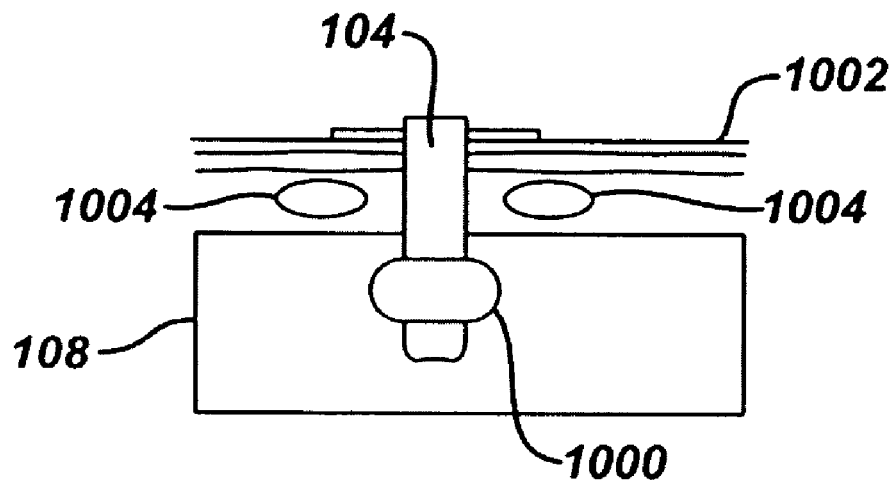
FIG. 10 is a diagrammatic representation of a first exemplary embodiment of a retention device in accordance with the present invention.

In accordance with one exemplary embodiment, the retention device comprises a balloon type retention element. FIG. 10 illustrates this exemplary balloon type retention element 1000. As illustrated, the air conduit 104 (FIG. 1) passes through the skin 1002, between ribs 1004 and into lung parenchymal tissue 108. The balloon element 1000 is secured to the air carrying conduit 104 by any suitable means, including adhesive, with the balloon in a deflated state, the conduit 104 and the balloon 1000 are positioned in the lung 108 of the patient. Once all elements are in the correct position, the balloon is inflated so that the conduit cannot be removed from the patient's lung until the balloon is deflated. The balloon 1000 may be inflated and deflated in any number of ways, including through a separate conduit positioned within the air carrying conduit 104. In an alternate exemplary embodiment, an additional balloon may be positioned outside of the lung 108 so that the air carrying conduit may not be moved in either direction. The balloon 1000 within the lung may be coated with one or more agents to prevent possible damage to or reaction by the lungs.

Figure 11:
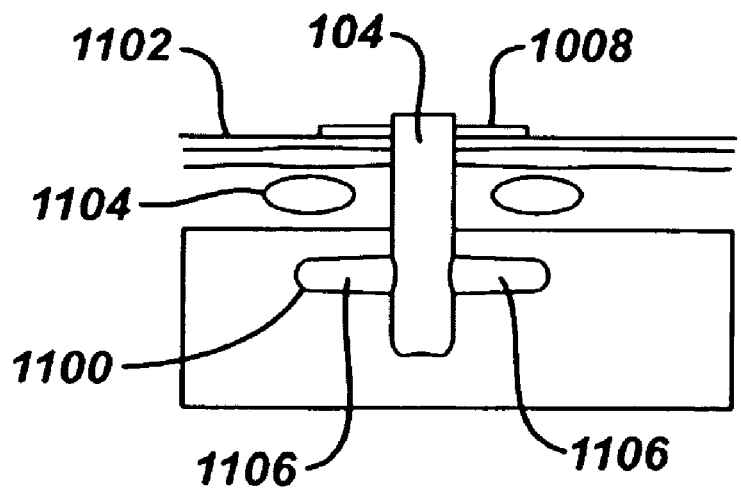
FIG. 11 is a diagrammatic representation of a second exemplary embodiment of a retention device in accordance with the present invention.

In accordance with another exemplary embodiment, the retention device comprises a hinged structure 1100 and an external retention component 1104. FIG. 11 illustrates the exemplary embodiment. As illustrated, the air conduit 104 passes through the skin 1102, between ribs 1104 and into lung parenchymal tissue 100. The hinged structure 1100 is attached to the air carrying conduit 104 such that during insertion each flap 1106 is substantially parallel to the air carrying conduit 104 and substantially perpendicular to the air carrying conduit 104 after placement. The flaps 1106 of the hinged structure 1100 may be controlled by spring type hinges, a separate spring structure similar to these utilized in toggle bolts or be constructed from a superelastic shape memory alloy such as nitinol. The flaps 1106 may comprise any suitable biocompatible material and be covered with one or more agents and/or material comprising agents to prevent possible damage to or reaction by the lungs. In this exemplary embodiment, a plate 1103 may be positioned around and affixed to the air carrying conduit 104 outside of the lung 108. This plate 1108 may comprise any suitable material and be attached to the skin 11102 by any suitable means, including adhesive. As in the above-described exemplary embodiment, a single component may be utilized. With the external devices, they can be constructed such that the air carrying conduits 104 may be detached for the reasons stated above, for example, maintenance.

The devices described herein provide a means for eliminating or substantially reducing trapped air in the lung or lungs by facilitating the flow of air via alternate pathways created through the pleura of the lung or lungs. However, by redirecting normal airflow through alternate passageways, the individual may find it somewhat more difficult to carry on certain activities or bodily responses requiring airflow through the native airways, i.e. the trachea. These activities and bodily responses may include speaking, coughing and throat clearing.

A potential solution to this problem may be achieved by the incorporation of a flow restrictor device or valve assembly for controlling the flow of air through the conduits of the collateral ventilation bypass system of the present invention. By controlling the airflow through the bypass system, increased air pressure in the lungs may be achieved so that additional air may be forced to flow or travel through the native airways. With this increase in pressure and additional air volume, the individual may be able to speak more easily by forcing more air to flow past the vocal chords, to cough and to clear his or her throat. In addition, an increase in pressure within the lung or lungs may increase gas exchange, thereby making the lung or lungs more efficient. Also, by utilizing a flow restrictor device or valve assembly to restrict or temporarily block the flow of air through the bypass system, the native air passages may be utilized more and thus remain healthy, operational and effective.

Essentially, a flow restrictor device or valve assembly would allow the individual to permanently or temporarily increase the pressure in the lungs and force more air through the native pathways in order to accomplish certain activities as briefly described above. The flow restrictor device or valve assembly may be manually operated by the individual, electronically operated by the individual or be completely automated. In the completely automated scenario, sensors would be utilized to sense certain biological parameters, such as the neurological impulse to cough, and provide feedback signals to control the flow restrictor device or valve assembly.

Figure 12A:
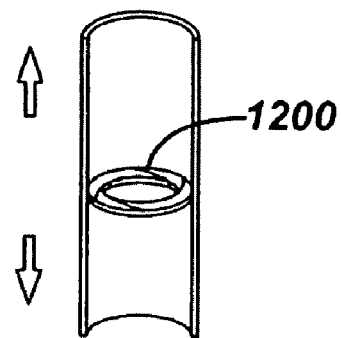
FIGS. 12a and 12b are diagrammatic representations of an iris valve assembly in accordance with the present invention.
Figure 12B:
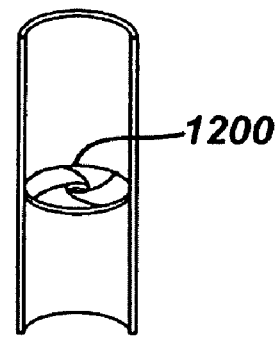

The flow restrictor device or valve assembly may comprise any suitable means for restricting or stopping the flow of air through a particular passageway or conduit. The flow restrictor device or valve assembly may comprise any suitable device that can be incorporated into any elements of the bypass system, for example, the conduits, and that may be readily adjustable to control the flow rate there through, for example, by changing the lumen diameter of the conduit. FIGS. 12a and 12b illustrate an exemplary iris valve assembly 1200. The iris valve assembly 1200 is similar in construction to the iris in a camera. The iris valve assembly 1200 may be positioned in any suitable location within the bypass system, for example, in conduit 104 of the exemplary bypass system illustrated in FIG. 1, in conduit 602 or conduit 606 of the exemplary bypass system illustrated in FIG. 6, and/or conduit 902 of the exemplary bypass system illustrated in FIG. 9. In FIG. 12a, the iris valve assembly is shown in the completely open state and in FIG. 12b, it is shown in the completely closed state. It is important to note that unlike a camera iris, this exemplary iris valve assembly may be partially opened or closed depending upon the desired degree of flow restriction. The iris valve assembly 1200 may be controlled manually or automatically by means known in the art.

Figure 13A:
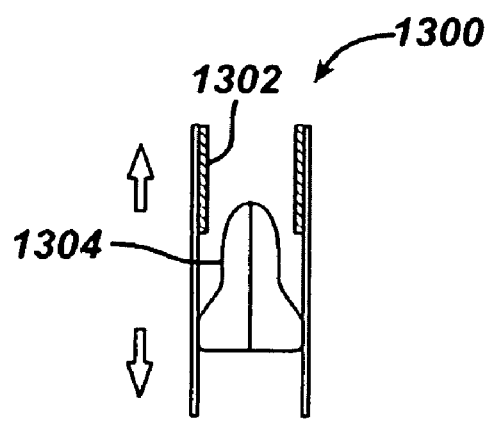
FIGS. 13a and 13b are diagrammatic representations of a duckbill valve assembly in accordance with the present invention.
Figure 13B:
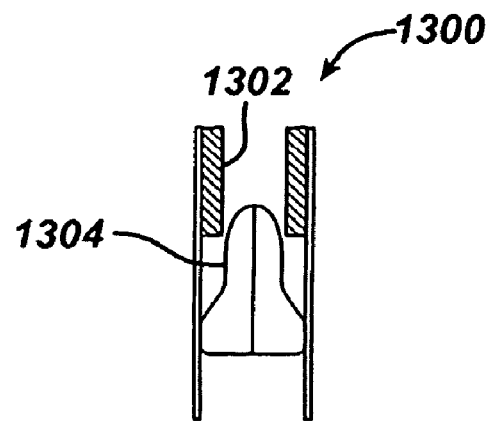

FIGS. 13a and 13b illustrate an exemplary duckbill valve assembly 1300. The duckbill valve assembly 1300 may be incorporated in any of the locations described above with respect to the iris valve assembly 1200. The exemplary duckbill valve assembly 1300 comprises a rotating collar 1302 and duckbill valve flaps 1304. A simple rotating motion causes the duckbill flaps 1304 to more within the rotating collar 1302, thereby fully opening the valve assembly 1300, fully closing the valve assembly 1300 or partially opening/closing the valve assembly 1300. FIG. 13a illustrates the valve assembly 1300 in the fully open position and FIG. 13b illustrates the valve assembly 1300 mostly closed. As with the previous exemplary embodiment, the duckbill valve assembly 1300 may be controlled manually or automatically by means known in the art.

Figure 14:
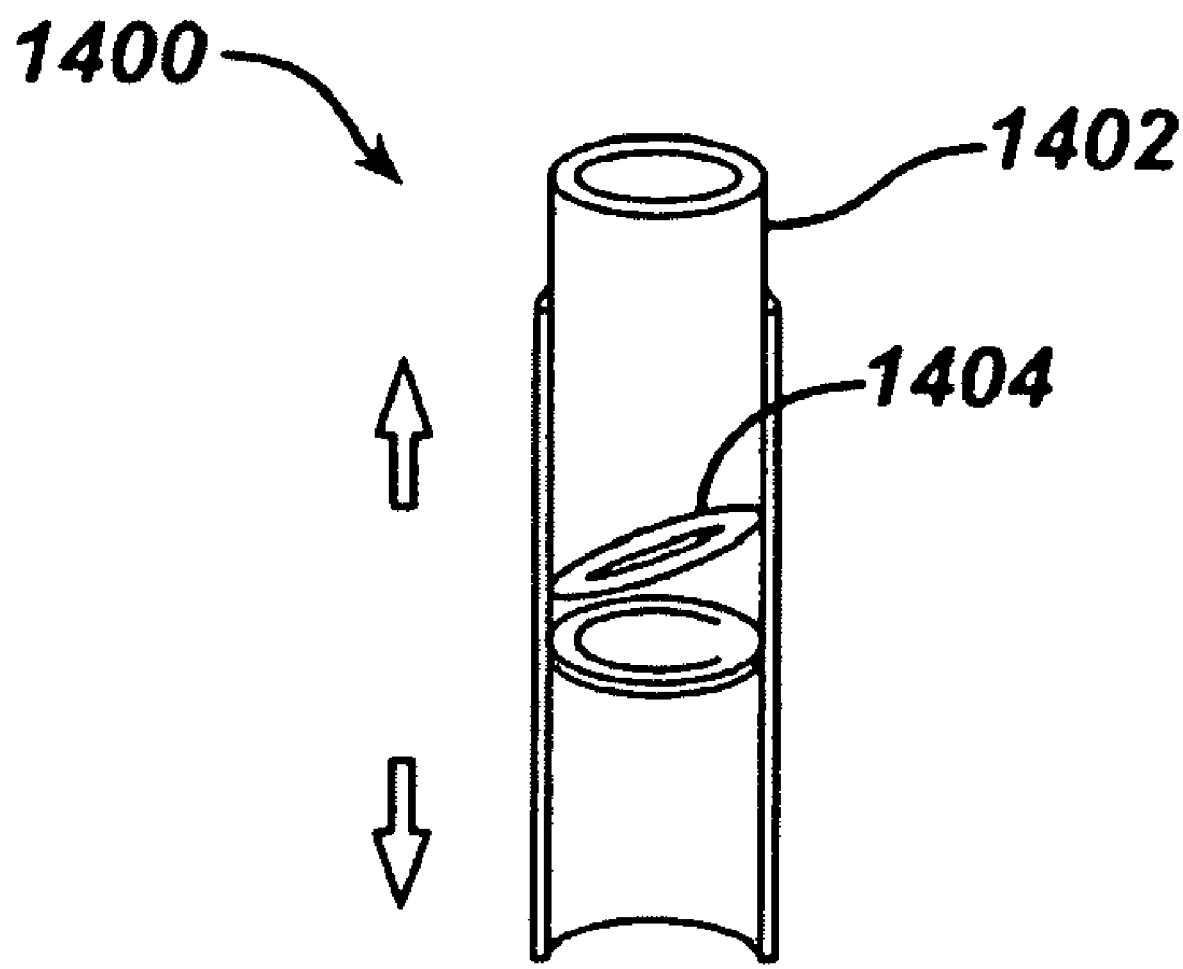
FIG. 14 is a diagrammatic representation of a flap valve assembly in accordance with the present invention.

FIG. 14 illustrates an exemplary flap valve assembly 1400. Once again, the flap valve assembly 1400 may be positioned at any suitable location within the bypass system. The exemplary flap valve assembly 1400 may simply comprise a rotating component 1402 and a one-way flap 1404. The position of the rotating component 1402 determines the amount the flap 1404 can open. As with the previous exemplary embodiment, the flap valve assembly 1400 may be controlled manually or automatically by means known in the art.

It is important to note that any type of valve assembly may be utilized in accordance with the present invention. The valve assembly should be easily controllable, reliable and easy to clean and maintain. In addition, the valve assemble should be readily accessible and easily positionable and sealable within the bypass system component.

In yet another alternate exemplary embodiment, the flow restrictor device or valve assembly may simply comprise a hand held attachment that covers the air exit port of the bypass system. Essentially anything that can be used to restrict to stop the flow of air from the lung or lungs may be utilized.

As stated above, initiating any of the devices described herein may be accomplished through a variety of means and methods. Rotating components in the devices described above may easily be incorporated into the bypass system elements and be physically initiated or actuated by the patient with simple movements. Alternately, an electrical, pneumatic or electromechanical system may also be incorporated into the bypass system so that the patient may simply depress a button or toggle a switch and actuate the valve assembly. With this type of system, the patient would not need to physically touch the bypass system too often, thereby reducing the risk of infection. It may also be beneficial or even necessary for patients who are physically unable to exert the amount of energy required to open and close the valve assembly.

In an alternate exemplary embodiment, the flow restrictor device or valve assembly may include a feedback control system, including sensors. With this type of system, the patient would not have to initiate any action. The sensors may be utilized to sense or measure a certain condition or conditions and provide a feedback signal to a controller, which in turns sends out a control signal to an actuator, for example, a solenoid connected to the valve, to open and or close the valve to a predetermined position or to a position sufficient to allow a certain event to occur. Detailed control laws may be written to cover a wide variety of sensors, a wide variety of sensed parameters and a wide variety of biological scenarios. The control system may be an analog or digital controller that requires low power and a small package that may be easily incorporated into the valve assembly or it may be a standalone package. The sensors may be hardwired to the controller or work via telemetry. Essentially, the control system, given a set of parameters, sends out control signals to an actuator that physically manipulates the valve assembly to achieve a desired result.

The control system may be an open loop control system wherein once something is sensed, actuation occurs, or it may be a closed loop system wherein precise control is achieved and maintained by periodic or continuous monitoring of the sensor or sensors. Either embodiment may include a patient override mechanism. In one exemplary embodiment, a sensor or sensors may be positioned to measure a change in flow, pressure and/or volume. Accordingly, a patient may signify a cough or talking sequence is about to occur by simply taking a deep breath. This would allow the sensor or sensors to sense the change in flow, pressure and/or volume and actuate the valve to change the flow of air out of the bypass system.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A ventilation bypass system for treating a lung of a patient comprising:
   a conduit adapted to pass through an artificial opening in a visceral membrane of a lung such that a proximal end of the conduit is external to the lung of the patient, a distal end of the conduit is inside the lung of the patient, and air present in the lung of the patient may exit the lung via the conduit;
   a seal around the artificial opening in the visceral membrane to prevent air from entering a pleural space around the lung at the artificial opening; and
   a flow-control device connected to the conduit which is adapted to adjustably restrict the exit of air from the lung through the conduit
   wherein the flow-control device is adapted to be controlled by the patient.

2. The ventilation bypass system of claim 1, wherein the flow-control device comprises an iris valve.

3. The ventilation bypass system of claim 1, wherein the flow-control device comprises a duckbill valve.

4. The ventilation bypass system of claim 1, wherein the flow-control device comprises a one-way flap valve.

5. The ventilation bypass system of claim 1, wherein the flow control device is configured for one of manual and electrical operation.

6. The ventilation bypass system of claim 1, wherein the flow control device is configured for automatic operation, except for a patient override.

7. The ventilation bypass system of claim 1, wherein the flow control device comprises:
   a sensor to assess a condition of the patient and generate an output in response to the condition;
   a valve and;
   a valve actuator which operates the valve to restrict the flow of air through the conduit in response to the output of the sensor.

8. The ventilation bypass system of claim 1, wherein the flow control device comprises:
   a switch adapted to be operated by the patient;
   a valve; and
   a valve actuator which operates the valve to restrict the flow of air through the conduit in response to the switch.

9. The ventilation bypass system of claim 1, wherein the flow control device is adapted to temporarily block the flow of air through the conduit.

10. A method of controlling air flow in a ventilation bypass system, wherein the method comprises:
    (a) selecting an adjustable flow control device connected to a conduit which is adapted to adjustably restrict the exit of air from the lung through the conduit whereby the actuation of the adjustable flow control device can restrict the exit of air from the lung through the conduit, which the adjustable flow control device is adapted to be controlled by the patient; and
    (b) implanting a conduit through an artificial opening in the visceral membrane of a lung such that a proximal end of the conduit is external to the lung of the patient, a distal end of the conduit is embedded within the lung of the patient, and air present in the lung of the patient exits the lung via the conduit; and
    (c) creating a seal around the artificial opening in the visceral membrane to prevent air from entering a pleural space around the lung from the artificial opening in the visceral membrane.

11. The method of claim 10, further wherein said step of (a) selecting comprises:
    (a1) selecting a control which automatically actuates the adjustable flow control device to temporarily restrict the exit of air from the lung through the conduit, except for a patient override.

12. The method of claim 11, wherein the step of (a1) selecting a control further comprising:
    (a2) selecting a control that can assess a condition of the patient with a sensor and generate an output in response to the condition; and
    (a3) selecting a control that can actuate the adjustable flow control device to temporarily restrict the exit of air from the lung through the conduit in response to the output of the sensor.

13. The method of claim 11, wherein the step of (a1) selecting a control further comprising:
    (a2) selecting a control that can assess a condition of the patient with an airflow sensor and generating an output in response to airflow; and
    (a3) selecting a control that can actuate the adjustable flow control device to temporarily restrict the exit of air from the lung through the conduit in response to the output of the airflow sensor.

14. The method of claim 11, wherein the step of (a1) selecting a control further comprising:
    (a2) selecting a control that can assess a condition of the patient with an air pressure sensor and generate an output in response to air pressure; and
    (a3) selecting a control that can actuate the adjustable flow control device to temporarily restrict the exit of air from the lung through the conduit in response to the output of the air pressure sensor.

15. A ventilation bypass system for treating a lung of a patient comprising:
    a conduit adapted to pass through an artificial opening in a visceral membrane of a lung such that a proximal end of the conduit is external to the lung of the patient, a distal end of the conduit is inside the lung of the patient, and air present in the lung of the patient may exit the lung via the conduit;
    a seal around the artificial opening in the visceral membrane to prevent air from entering a pleural space around the lung at the artificial opening; and
    a flow-control device connected to the conduit which is adapted to adjustably restrict the exit of air from the lung through the conduit
    wherein the flow-control device is automatically controlled.

16. The ventilation bypass system of claim 15, wherein the flow-control device comprises an iris valve.

17. The ventilation bypass system of claim 15, wherein the flow-control device comprises a duckbill valve.

18. The ventilation bypass system of claim 15, wherein the flow-control device comprises a one-way flap valve.

19. The ventilation bypass system of claim 15, wherein the flow control device comprises:
    a sensor to assess a condition of the patient and generate an output in response to the condition;
    a valve and;
    a valve actuator which operates the valve to restrict the flow of air through the conduit in response to the output of the sensor.

* * * * *